US007741128B2

(12) United States Patent
Su

(10) Patent No.: US 7,741,128 B2
(45) Date of Patent: Jun. 22, 2010

(54) COOPERATIVE REPORTER SYSTEMS, COMPONENTS, AND METHODS FOR ANALYTE DETECTION

(75) Inventor: Wei Wen Su, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 688 days.

(21) Appl. No.: 11/440,215

(22) Filed: May 23, 2006

(65) Prior Publication Data

US 2008/0064025 A1 Mar. 13, 2008

Related U.S. Application Data

(60) Provisional application No. 60/683,921, filed on May 23, 2005, provisional application No. 60/778,991, filed on Mar. 1, 2006.

(51) Int. Cl.
*G01N 33/566* (2006.01)
*G01N 33/563* (2006.01)
*G01N 33/00* (2006.01)

(52) U.S. Cl. ....................... 436/501; 436/512; 436/513; 436/86

(58) Field of Classification Search ....................... None
See application file for complete search history.

(56) References Cited

U.S. PATENT DOCUMENTS

| | | | |
|---|---|---|---|
| 5,981,199 | A | 11/1999 | Ueda et al. |
| 6,162,903 | A | 12/2000 | Trowern et al. |
| 6,822,075 | B2 | 11/2004 | Björck et al. |
| 6,884,629 | B2 | 4/2005 | Gore et al. |
| 2003/0073149 | A1 | 4/2003 | Archer |
| 2004/0110245 | A1 | 6/2004 | Nagamune et al. |
| 2006/0068502 | A1 | 3/2006 | Su |

FOREIGN PATENT DOCUMENTS

| | | |
|---|---|---|
| EP | 1 382 965 | 1/2004 |
| WO | WO 2005033130 | 4/2005 |
| WO | WO 2005/089409 | 9/2005 |
| WO | WO 2005/042695 | 12/2005 |

OTHER PUBLICATIONS

Akerstrom and Bjorck, Protein L: An Immunoglobulin Light Chain-binding Bacterial Protein: Characterization of Binding and Physicochemical Properties. J Biol Chem. vol. 264, No. 33, Issue of Nov. 25, pp. 19740-19746 1989.*

Nielsen, et al. A homogeneous fluorescence polarization assay for detection of antibody to *Brucella abortus*. Journal of Immunological Methods 195 (1996) 161-168.*

(Continued)

*Primary Examiner*—Mary E Mosher
*Assistant Examiner*—Stuart W Snyder
(74) *Attorney, Agent, or Firm*—Davis Wright Tremaine LLP

(57) ABSTRACT

The present invention relates to methods and compositions to detect analytes in a sample using antibody molecules that are transformed into nanoscale "self-signaling" biosensors. It relates in particular to those methods and compositions that provide for single-step detection of target analytes without the need for labor-intensive steps necessary in conventional assays.

19 Claims, 14 Drawing Sheets

OTHER PUBLICATIONS

Szollo9si, et al. Cytometry (Communications in Clinical Cytometry) 34:159-179 (1998).*

Kurstak, E. Progress in enzyme immunoassays: Production of reagents, experimental design, and interpretation. Bull. WHO. 1985; 63(4):793-811.*

Åkerström and Björck. Protein L: An Immunoglobulin Light Chain-binding Bacterial Protein: Characterization of Binding and Physicochemical Properties. J. Biol. Chem. 1989; 264(33):19740-1976.*

Aoki, et al. Construction of a fusion protein between protein A and green fluorescent protein and its application to Western blotting, FEBS Letters. 1996; 384:193-197.*

Rogers, et al. Immunohistochemical Localization of Feline Immunodeficiency Virus Using Native Species Antibodies. Am. J. Pathol. 2002; 161(4): 1143-1151.*

Green, NM Avidin and Streptavidin. Met. Enzymol. 1990; 184:51-67.*

Arai, et al. Demonstration of a Homogeneous Noncompetitive Immunoassay Based on Bioluminescence Resonance Energy Transfer. Anal. Biochem. 2001; 289: 77-81.*

Adams, S.R. et al. 2002. New biarsenical ligands and tetracysteine motifs for protein labeling in vitro and in vivo: synthesis and biological applications. *J Am Chem Soc*. 124(21):6063-76.

Chin, J.W. et al. "Addition of a photocrosslinking amino acide to the genetic code of *Escherichia coli*," 2002(a). *Proc Natl Acad Sci U S A* 99:11020-11024.

Chin, J.W. et al., "In Vivo Photocrosslinking with Unnatural Amino Acid Mutagenesis," 2002(b). *Chembiochem* 3:1135-1137.

Clamme, J.-P. and Ashok A. Deniz. 2005. Three-Color Single-Molecule Fluorescence Resonance Energy Transfer. *ChemPhysChem* 6: 74-77.

De Chateau, M. et al., <<On the Interaction between Protein L and Immunoglobulins of Various Mammalian Species, >> 1993. *Scand J Immunol* 37:399-405.

Deo, S.K. 2004. Exploring bioanalytical applications of assisted protein reassembly. *Anal Bioanal Chem* 379: 383-390.

Farrell, I.S. et al., "Photo-cross-linking interacting proteins with a genetically encoded benzophenone," 2005. *Nat Methods* 2:377-384.

Galarneau, A. et al., β-Lactamase protein fragment complementation assays as in vivo and in vitro sensors of protein-protein interactions, >> 2002. *Nat Biotechnol* 20:619-622.

Galperin, E. et al. 2004. Three-chromophore FRET microscopy to analyze multiprotein interactions in living cells. *Nature Methods* 1(3): 209-217.

Gao, W. et al. 2003. Novel Fluorogenic Substrates for Imaging beta-Lactamase Gene Expression. *J. Am. Chem. Soc.* 125(37):11146-11147.

Kastern, W. et al. 1992. Structure of peptostreptococcal protein L and identification of a repeated immunoglobulin light chain-binding domain. *J. Biol. Chem.* 267, 12820-5.

Komiya, N. et al., << Homogenous sandwich immunoassay based on the enxymatic complementation induced by single-chain Fv fragments, >> 2004. *Anal Biochem* 327:241-246.

Li, F. et al., << Homogenous Noncompetitive Immunoassay Based on the Energy Transfer Between Fluoro-labeled Antibody Variable Domains (Open Sandwich Fluoroimmunoassay), 1999. *Biotechniques* 27:738-742.

Lichlyter, D.J et al., << Development of a novel FRET immunosensor technique, >> 2003. *Biosens Bioelectron* 19:219-226.

Lindhout, D.A. et al. 2004. NMR solution structure of a highly stable de novo heterodimeric coiled-coil. *Biopolymers* 75(5):367-75.

Medintz, I.L. et al., << Self-assembled nanoscale biosensors based on quantum dot FRET donors, >> 2003. *Nat Mater* 2:630-638.

Ohiro, Y. et al., << A Homogenous and Noncompetitive Immunoassay Based on the Enhanced Fluorescence Resonance Energy Transfer by Leucine Zipper Interaction, >> 2002. *Anal Chem* 74:5786-5792.

Presta, L. 2003. Antibody engineering for therapeutics. *Current Opinion in Structural Biology* 2003, 13:519-525.

Renard, M. et al., „Knowledge-based Design of Reagentless Fluorescent Biosensors from Recombinant Antibodies, 2002. *J Mol Biol* 318:429-442.

Renard, M. et al., "Improving the Sensitivity and Dynamic Range of Reagentless Fluorescent Immunosensors by Knowledge-Based Design," 2004. *Biochemistry* 43:15453-15462.

Selvin, P.R., "Fluorescence Resonance Energy Transfer," 1995. *Methods Enzymol* 246:300-334.

Svensson, H.G. et al., << Contributions of Amino Acid Side Chains to the Kinetics and Thermodynamics of the Bivalent Binding of Protein L to Ig κ Light Chain, 2004. *Biochemistry* 43:2445-2457.

Ueda, H. et al., << An optimized homogeneous noncompetitive immunoassay based on the antigen-driven enzymatic complementation, >> 2003. *J Immunol Methods* 279:209-218.

Ueda, H., <<"Open Sandwich Immunoassay: a Novel Immunoassay Approach Based on the Interchain Interaction of an Antibody Variable Region."2002. *Journal of Bioscience and Bioengineering* 94:614-619.

Vet et al., "Multiplex detection of four pathogenic retroviruses using molecular beacons," 1999. Multiplex detection of fourpathogenic retroviruses using molecular beacons. *PNAS* 96(11):6394-6399.

Watrob, H.M. et al., << Two-Step FRET as a Structural Tool, >> 2003. Two-Step FRET as a Structural Tool. *J. Am. Chem. Soc.* 125:7336-7343.

Wehrman, T. et al., "Protein-protein interactions monitored in mammalian cells via complementation of β-lactamase enzyme fragments," 2002. *Proc Natl Acad Sci U S A* 99:3469-3474.

Yang, X. et al., << Homogeneous enzyme immunoassay modified for application to liminescence-based biosensors, >> 2005. *Anal Biochem* 336:102-107.

Zhang, W.X. et al., << Time-resolved Forster resonance energy transfer assays for the binding of nucleotide and protein substrates to p38α protein kinase, 2005. *Anal Biohem* 343:76-83.

Selvin, Paul R. 2000. "The renaissance of fluorescence resonance energy transfer." *Nature Structural Biology* 7(9): 730-734.

* cited by examiner

COOPERATIVE REPORTER SYSTEMS, COMPONENTS, AND METHODS FOR ANALYTE DETECTION

CROSS-REFERENCE TO RELATED APPLICATIONS

The present application claims priority to U.S. Provisional Application No. 60/683,921, filed on May 23, 2005, and to U.S. Provisional Application No. 60/778,991, filed on Mar. 1, 2006.

BACKGROUND OF THE INVENTION

1. Field of the Invention

Embodiments of the present invention relate to methods and compositions to detect analytes in a sample using antibody molecules that are transformed into nanoscale "self-signaling" biosensors, in particular those methods and compositions that provide for single-step detection of target analytes without the need for labor-intensive steps necessary in conventional assays.

2. Description of the Related Art

Immunoassays are based on specific interactions between antibodies and antigens. They are indispensable in modern clinical diagnostics, drug screening practices, and medical research in general. Among the immunoassay formats, enzyme-linked immunosorbent assay (ELISA), lateral-flow immunoassays, and Western-blot assays are most widely used. ELISA and Western-blot techniques require multiple cycles of incubation/washing steps and are hence laborious and prone to operator error. Lateral-flow immunoassays, such as dip-stick type assays, generally provide faster detection but are not as sensitive or accurate as conventional ELISAs. All of these assays are conducted using the heterogeneous format, i.e. they all require immobilization of antibodies or antigens onto a solid surface. In comparison, homogeneous assays, in which no antibody/antigen immobilization is necessary, provide many important advantages over the heterogeneous assays. First and foremost, homogeneous immunoassays enable direct detection in solution, in a "mix and detect" manner, without needing multiple incubation steps or additional signal-generating elements, and hence greatly accelerate assay throughputs while preserving assay sensitivity and specificity. Furthermore, it is preferred to conduct the homogeneous assays in the non-competitive format as opposed to competitive format since the former is in general more sensitive by orders of magnitude [Ohiro et al. 2002, herein incorporated by reference in its entirety]. Having an effective and universal assay platform that allows homogeneous solution-phase non-competitive immunoassays is particularly valuable when interrogating a large number of samples since such format is more amenable to automation using robotic liquid-handling systems prevalent in modern high-throughput screening applications. However, a key technical challenge has been the development of a simple and effective reporting mechanism to signal the antigen-antibody interaction in solution.

SUMMARY OF THE INVENTION

The present invention provides, in some embodiments, a method of sensing an analyte, including the steps of: providing a biological sample; contacting the sample with at least one cooperative reporter reagent for detecting the analyte, wherein the reporter reagent can include an affinity component, a linking component, and a cooperative reporter component; determining presence or absence of a signal from the system, wherein the signal can be indicative of presence of the analyte in the sample; and sensing the analyte based upon presence or absence of the signal wherein the signal can be not detected above background in the absence of the analyte.

In some embodiments, the analyte to be detected can be, for example, a material or a part thereof selected from the group consisting of a protein, a peptide, an antigen, an antibody, a lectin, a lectin-binding carbohydrate, a disease marker, a cytokine, a cytokine receptor, a hormone, a hormone receptor, a cell adhesion molecule, a cell adhesion molecule ligand, a nucleic acid, a sugar chain, a lipid, a cell, a virus, an intracellular organelle, a small molecule, a low molecular weight compound, and the like.

Likewise, in some embodiments, the linking component can be a Protein L linker, wherein the Protein L linker can include Protein L or a fragment or derivative thereof. The Protein L linker can include a modification permitting or enhancing chemical attachment of the derivative to the affinity component. Further, the Protein L linker can include a modification permitting or enhancing chemical attachment of the derivative to the reporter component. The Protein L linker can include a polypeptide having all or part of the sequence of SEQ ID NO:7, 8, 9, or 10 (nucleotide sequences of SEQ ID NO:2, 3, 4, or 5, respectively).

In some embodiments, the affinity component can include an antibody or a fragment or derivative thereof. The reporter component can include, for example, a fluorescent material, an enzyme, an enzyme fragment, an enzyme subunit, a receptor, a ligand, a fluorescent protein, a luminescent protein, a non-protein fluorophore, a non-protein chemiluminescent compound, a fluorophore-labeled protein, a fluorescent nanocrystal, a fluorescent chelate, a photosensitizer dye, a fluorescence quencher, and the like.

The linkage of the Protein L linker to the reporter component can include a chemical linkage. The Protein L linker can be linked to the reporter component as a fusion protein. The linkage of the Protein L linker to the reporter component can include a noncovalent interaction. Further, the linkage of the Protein L linker to the reporter component can include a biotin-streptavidin conjugation. The linkage of the Protein L linker to the affinity component can include self-assembly. The self assembly can be via hydrogen bonding, salt bridging, or a combination thereof. The linkage of the Protein L linker to the affinity component can include photocrosslinking.

In various embodiments, detection of the analyte can be carried out in a homogeneous system. Likewise, in various embodiments, the signal can be an optical signal such as, for example, an optical signal generated as a result of FRET, LRET, BRET, enzyme fragment complementation, TR-FRET, Luminescent Oxygen Channeling, and the like. In some embodiments, detection of the signal does not require instrumentation.

In some embodiments, the contacting step can include contacting the sample with at least two cooperative reporter reagents, wherein the cooperative reporter reagents in combination constitute a multiplex cooperative reporter system, wherein generation of a signal can include interaction between the two cooperative reporter reagents without binding between the linking components of the at least two reagents. In some embodiments, each of the at least two cooperative reporter reagents can include a distinct affinity component, such that the distinct affinity components each have an affinity for a different portion of a same analyte.

Additional embodiments of the invention provide a cooperative reporter system for detecting an analyte, including at least one cooperative molecular reagent, the reagent including an affinity component, a linking component, and a cooperative reporter component, wherein the reporter component cooperates with a second reporter component to produce a signal, and wherein the signal is not detected above background in absence of the analyte. In some embodiments, the second reporter component is associated with a second cooperative molecular reporter agent, while in other embodiments, the second reporter component is not associated with a second cooperative molecular reporter agent. In some embodiments, the system can include at least two cooperative molecular reagents, wherein the linking component of a first molecular reagent lacks any affinity above background for the linking component of a second molecular reagent in the system. In some embodiments, binding or interaction between the at least two molecular reagents to the analyte places the reporter components in close proximity.

In some embodiments, the linking component can include a Protein L linker, wherein the Protein L linker can include Protein L or a fragment or derivative thereof. Likewise, the Protein L linker can include a modification permitting or enhancing chemical attachment of the derivative to the affinity component. The Protein L linker can include a modification permitting or enhancing chemical attachment of the derivative to the reporter component. The Protein L linker can include a polypeptide or portion thereof having the sequence of SEQ ID NO: 7, 8, 9, or 10 (nucleotide sequences of SEQ ID NO:2, 3, 4, or 5, respectively). The affinity component can include an antibody or a fragment or derivative thereof. The reporter component can include, for example, a fluorescent material, an enzyme, an enzyme fragment, an enzyme subunit, a receptor, a ligand, a fluorescent protein, a luminescent protein, a non-protein fluorophore, a non-protein chemiluminescent compound, a fluorophore-labeled protein, a fluorescent nanocrystal, a fluorescent chelate, a photosensitizer dye, a fluorescence quencher, and the like. The linkage of the Protein L linker to the reporter component can include, for example, a chemical linkage, can be as a fusion protein, can include a noncovalent interaction, a biotin-streptavidin conjugation, and the like. Linkage of the Protein L linker to the affinity component can include, for example, self-assembly, photocrosslinking and the like.

In further embodiments of the invention there is provided a biosensor for detecting an analyte including: an affinity moiety; a cooperative reporter; and a linking component including a Protein L linker, wherein the Protein L linker can include Protein L or a fragment or derivative thereof. In some embodiments, the biosensor can further include one or more additional cooperative reporters. The affinity moiety can include, for example, an antibody or fragment or derivative thereof. The cooperative reporter can include, for example, a fluorescent material, an enzyme, an enzyme fragment, an enzyme subunit, a receptor, a ligand, a fluorescent protein, a luminescent protein, a non-protein fluorophore, a non-protein chemiluminescent compound, a fluorophore-labeled protein, a fluorescent nanocrystal, a fluorescent chelate, a photosensitizer dye, a fluorescence quencher, and the like. The Protein L linker can include a modification permitting or enhancing chemical attachment of the derivative to the affinity component. The biosensor of claim 39, wherein the Protein L linker can include a modification permitting or enhancing chemical attachment of the derivative to the reporter component. The Protein L linker can include a polypeptide or fragment thereof including all or part of the sequence of SEQ ID NO: 7, 8, 9, or 10 (nucleotide sequences of SEQ ID NO:2, 3, 4, or 5, respectively). The linkage of the Protein L linker to the reporter component can include, for example, a chemical linkage, can be as a fusion protein, can include a noncovalent interaction, a biotin-streptavidin conjugation, and the like. Linkage of the Protein L linker to the affinity component can include, for example, self-assembly, photocrosslinking and the like.

DETAILED DESCRIPTION OF THE PREFERRED EMBODIMENT

Embodiments of the present invention provide novel synthetic proteins that enable convenient site-specific covalent or non-covalent coupling of reporter molecules to standard antibodies, for rapid and sensitive single-step homogeneous non-competitive immunoassays. Such assay format allows direct detection in solution without needing multiple incubation steps or additional signal-generating elements, as required by conventional immunoassays, and thus greatly accelerates assay throughputs while preserving assay sensitivity and specificity. Accordingly, embodiments of the invention provide technology that transforms off-the-shelf antibodies for use in an assay format that is faster and simpler then the conventional ELISAs.

Instead of engineering the antibody itself, embodiments of the invention provide a novel approach to couple an engineered reporter (the biomolecular adapter) to a specific site of the antibody to transform the antibody molecules into self-reporting reagentless molecular biosensors that are well suited for homogeneous non-competitive and competitive immunoassays. A beneficial aspect involves coupling signal-generating groups to antibodies via the biomolecular adapter to generate a detectable signal upon binding of the antibodies to their target antigens, via fluorescence resonance energy transfer (FRET) [Selvin 1995, herein incorporated by reference in its entirety] or enzyme fragment complementation [Wehrman et al. 2002, Galarneau et al. 2002, each of the foregoing which is incorporated herein by reference in its entirety]. The assay can be done in a "mix and detect" manner, without requiring multiple washing steps. This allows development of simple homogeneous assays particularly well adapted to high throughput applications.

Figure 1:
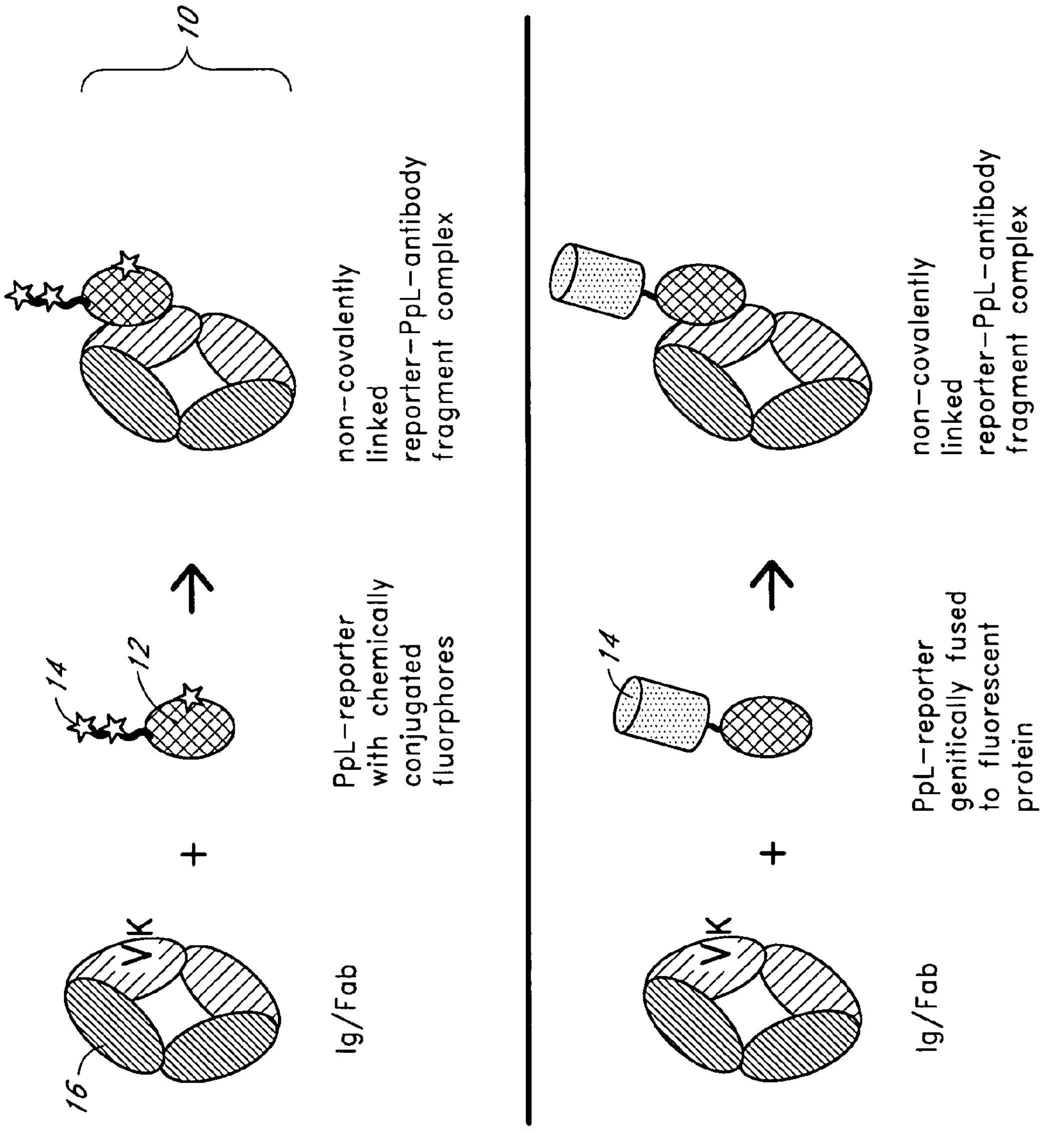
FIG. 1 depicts schematically a process to create a molecular biosensor containing a self-assembled non-covalently linked reporter-Protein L-antibody fragment complex.
Figure 2:
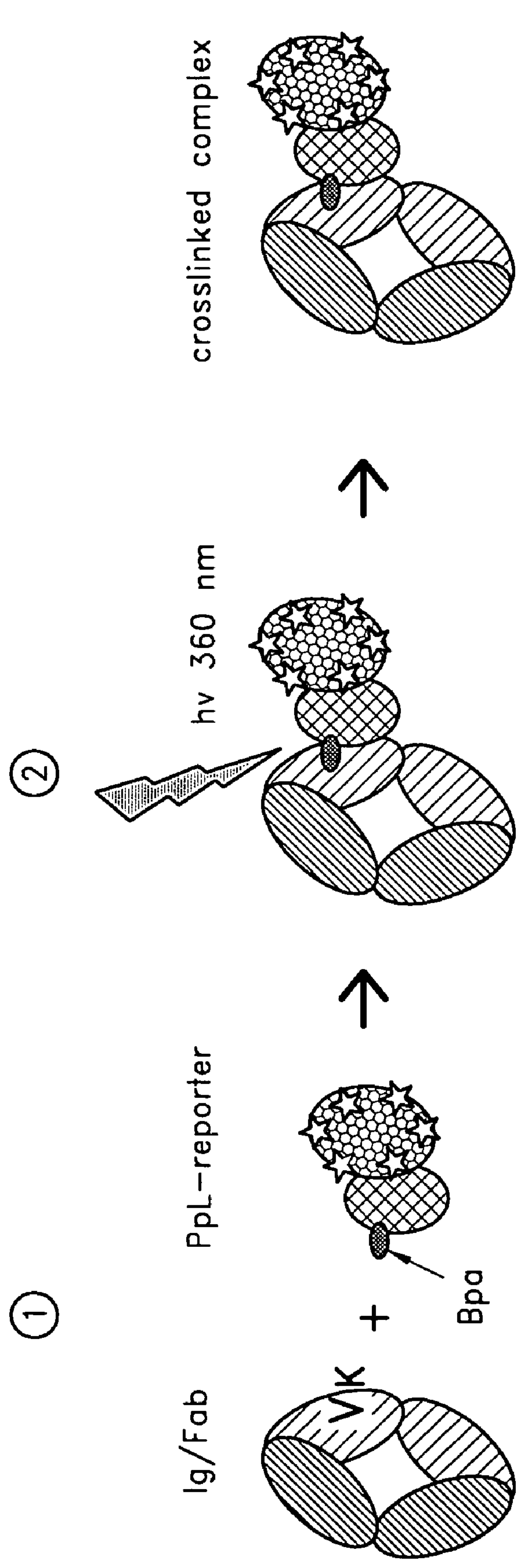
FIG. 2 depicts schematically a process to create a molecular biosensor containing a covalently linked reporter-Protein L-antibody fragment complex.

A key technical challenge that is overcome in aspects of the present invention is to develop a simple and effective reporting mechanism to signal the antigen-antibody interaction in solution. This can be accomplished via a novel approach to transform antibody molecules into self-reporting molecular biosensors, by means of a biomolecular adapter that is derived from the *Peptostreptococcus magnus* Protein L (PpL) immunoglobulin (Ig)-binding domains. Such adapter enables convenient site-specific covalent coupling of cargo molecules (such as reporter groups or therapeutic agents) to antibodies or antibody fragments. The biomolecular adapter can be used in a variety of ways for homogeneous immunoassays. The PpL Ig-binding domain (e.g. the B1 domain) is subject to a combination of genetic and chemical modifications to attach a fluorescent reporter and allowed to be self assembled and covalently or noncovalently captured by an immunoglobulin (Ig) kappa type variable light chain. The functionalized PpL-Ig protein complex is then used in a FRET (fluorescence resonance energy transfer) based homogeneous non-competitive immunoassay. For example, when two antibody molecules, one labeled with a PpL-FRET donor, and the other with a PpL-FRET acceptor, both bind the target molecule, the FRET donor and acceptor come in close vicinity of each other to cause FRET Embodiments of the invention utilize a biomolecular adapter based on the *Peptostreptococcus magnus* Protein L (PpL) domains. *P. magnus* PpL contains five homologous Ig-binding domains (B1-B5) (Kastern et al. 1992, herein incorporated by reference in its entirety). These domains are small in size (72-76 amino acid residues) and have a high affinity (nM range) for the kappa type variable light chain (Vκ) of immunoglobulins [De Chateau et al. 1993, herein incorporated by reference in its entirety]. Interestingly and importantly, the binding of PpL to Vκ does not impair the binding affinity of the antibody [De Chateau et al. 1993]. Wild-type PpL B1 domain binds human, baboon, guinea pig, mouse, rat, and pig IgG with high affinity ($K_D$ in the nM range), and binds rabbit, horse, and goat IgG with less affinity ($K_D$ in the sub-μm range) [De Chateau et al. 1993]. Referring to the drawings, a molecular biosensor 10 can be constructed by non-covalently or covalently coupling a PpL-based linking component 12 that is linked to a reporter component 14 to an affinity component 16. The reporter component 14 may be tethered to the linking component 12 by means such as, for example, genetic fusion or chemical conjugation. In some embodiments of the present invention, reporter-conjugated PpL-B1 domain is non-covalently coupled to an antibody or antibody fragment through a self-assembly process via specific hydrogen bonds and salt bridges between PpL and the antibody. This process is illustrated in FIG. 1. In other embodiments of the present invention, a two-step process to covalently link a reporter-conjugated PpL-B1 domain to an antibody or antibody fragment (e.g. Fab or Fv) near the antigen-binding site is performed. In the first step, a mutated and reporter-conjugated PpL-B1 domain is allowed to form a complex with an antibody via PpL's unique site-specific Ig-binding property. To accomplish this, two important mutations are introduced into the PpL-B1 domain. First, PpL B1 domain is mutated at one of its two immunoglobulin-binding sites (which have been reported to exhibit similar Ig-binding affinities [Svensson et al. 2004, herein incorporated by reference in its entirety]) to enable site-specific biotinylation. The biotinylated PpL and a reporter-labeled streptavidin are then allowed to self-assemble into a tightly bound protein complex. This procedure serves two important functions: (1) to abolish one of PpL's two Ig-binding sites, and (2) to attach a reporter group to the PpL B1 domain. In the second step, another mutation is introduced to allow introduction of an unnatural photocrosslinking amino acid residue (p-benzoyl-L-phenylalanine; Bpa) into PpL-B1 near its Ig-binding site using a technique developed in Peter Schultz's group that involves the use of an engineered orthogonal aminoacyl-tRNA synthetase/tRNA pair for the in-vivo incorporation of Bpa into proteins in Escherichia coli in response to the amber codon, TAG [Chin et al. 2002(a), Chin et al. 2002(b), Farrell et al. 2005, each of the foregoing which is herein incorporated by reference in its entirety]. After the mutated and reporter-coupled PpL-B1 domain is allowed to self assemble with the Ig, the protein complex is exposed to long-wavelength UV light (360 nm) to photocrosslink the complex to form a covalently-linked structure. This two-step process is illustrated in FIG. 2.

Figure 3:
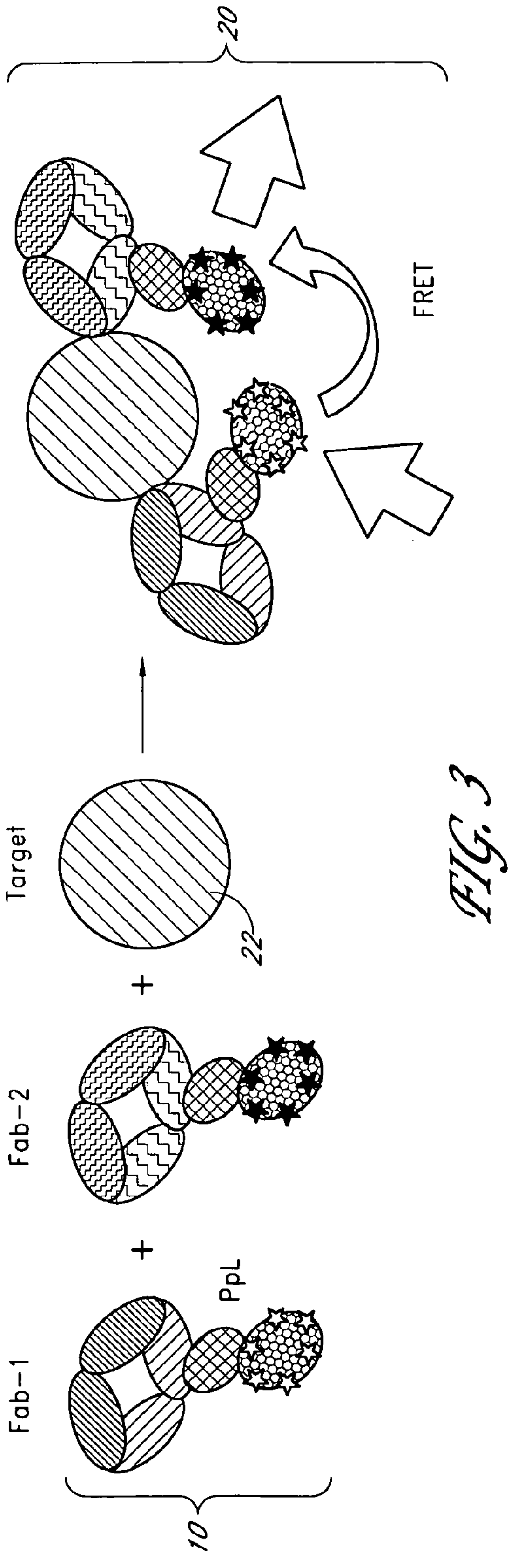
FIG. 3 illustrates a homogeneous non-competitive immunoassay using a cooperative reporter system based on the molecular biosensor containing a reporter-Protein L-antibody fragment complex.
Figure 4:
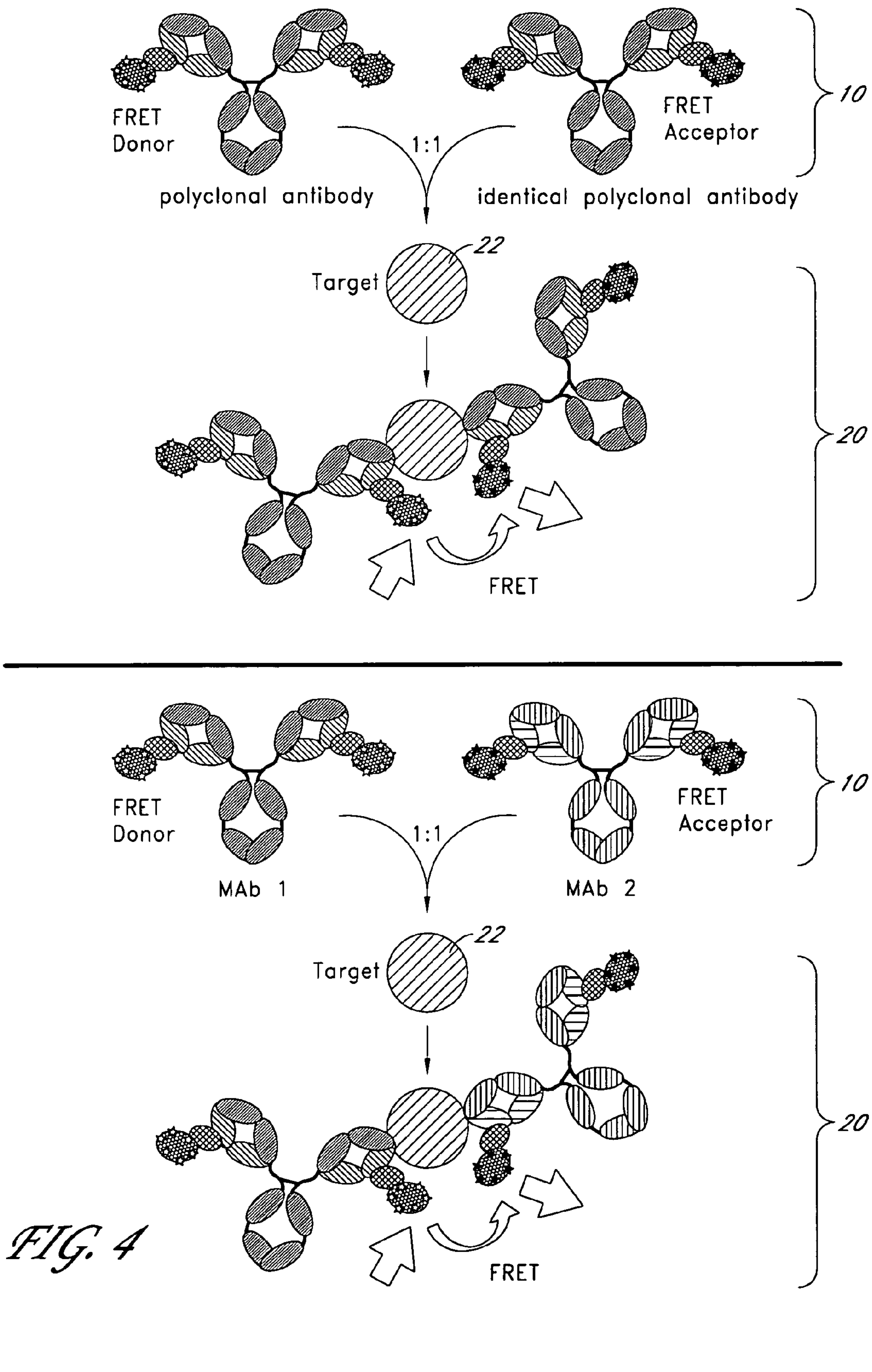
FIG. 4 shows a homogeneous non-competitive assay using a cooperative reporter system based on the molecular biosensor containing a reporter-Protein L coupled to whole antibody molecules.

In the present invention, cargo molecules can be linked to antibodies by antibody-binding proteins such as, for example, Protein A or Protein G. However, Protein L B1 domain is preferred over other antibody-binding proteins such as Protein A or Protein G for two reasons: 1) PpL binds to the antibody close to the antigen-binding site (without affecting antigen binding), shortens the distance of the FRET pair when the labeled antibodies bind the target and enhances the FRET signal; 2) PpL binds whole IgG's as well as Fab and Fv fragments or library-selected recombinant single-chain Fv's, broadening the choice of highly specific and sensitive detectors available. As illustrated in FIG. 3, reporter-PpL molecular adapters are coupled to Fab fragments in developing a non-competitive homogeneous immunoassay. One can also apply the reporter-PpL molecular adapter to whole Ig molecules in developing the homogeneous immunoassay, as depicted in FIG. 4. To prevent Ig-mediated protein oligomerization and crosslinking, one can apply a higher concentration of the PpL-Ig complex relative to the target. A unique FRET technique called time-resolved FRET (or TR-FRET) that utilizes a luminescent europium chelate as donor and allophycocyanin or an organic dye, Cy5, as acceptor, can provide over 50 fold improvement in detection sensitivity over steady-state FRET measurement using conventional donor/acceptor pairs [Selvin 1995, herein incorporated by reference in its entirety].

While there are various reports on competitive homogeneous immunoassays, examples of non-competitive homogeneous immunoassays are scarce. Bedouelle and coworkers [Renard et al. 2002, Renard et al. 2004, each of the foregoing which is herein incorporated by reference in its entirety] reported an approach to transform the variable fragment (Fv) of an antibody into a reagentless fluorescent biosensor by mutating a residue into a cysteine near the antigen-binding site and then conjugated an environment-sensitive fluorophore to the cysteine residue. Antigen binding reportedly generated a measurable variation in the fluorescence intensity of the conjugate. Ueda et al [Ueda et al. 1999, Ohiro et al. 2002, Ueda et al. 2003, Komiya et al. 2004, Ueda et al. 2004, each of the foregoing which is herein incorporated by reference in its entirety] reported a novel homogeneous sandwich immunoassay, in which two scFvs or a pair of variable heavy chain (VH) and light chain (VL) fragments, each labeled with a fluorescent protein, chemical fluorophore, or an enzyme fragment are brought together in the presence of a target in solution and a signal is generated as a result of FRET or enzyme fragment complementation. In FRET, a fluorescent donor molecule transfers energy to an acceptor molecule via a nonradiative dipole-dipole interaction. Upon energy transfer, the donor's lifetime and quantum yield are reduced, while the acceptor fluorescence is increased, or sensitized. Such energy transfer depends on the distance and orientation between the donor and acceptor. With VH/VL fragment complementation, an obvious limitation is that it requires a sufficiently weak VH/VL interaction in the absence of the antigen. Furthermore, with VH/VL fragment complementation, the binding affinity is considerably compromised [Ueda et al. 1999, Ueda et al. 2003]. The approaches put forward by Bedouelle et al and Ueda et al are both limited to recombinant antibody fragments since manipulation of the antibodies to introduce the reporter moiety requires modification of the genes encoding the antibody/fragments. As a result, these approaches cannot be adapted for non-recombinant antibodies which make up the majority of the antibodies used in immunoassays.

Embodiments of the present invention provide methods and compositions for use in detecting an analyte or analytes 22 in a sample. A novel approach is used to link at least one reporter molecule (R) via an adapter molecule to a specific site of an affinity moiety (A), thus transforming the affinity moiety into a self-reporting, reagentless, molecular biosensor that is well suited for assays.

In a preferred embodiment, the biosensor is used in a homogeneous assay. In another embodiment, the biosensor is used in a heterogeneous assay. For example, where the assay takes place in a heterogeneous environment, one or more molecular biosensors can be immobilized on a solid surface, and detection of analyte takes place by mixing the sample with the molecular biosensor with or without subsequent washing steps before signal analysis.

In embodiments of the present invention, signal analysis involves detection of signal. Detectable signals involve, for example, generation of signal above background, alteration of signal emission, alteration of signal magnitude, alteration of signal frequency, alteration of signal wavelength, signal quenching, signal interference, and the like. Detectable signals also include, for example, signals that are bioluminescent, chemiluminescent, fluorescent, and the like. Embodiments of the invention can employ a detectable signal that results from, for example, a change or formation of detectable properties in enzymatic reaction products; a change in phase, precipitation of solids, change in color or optical property of the sample, and the like.

The sample to be analyzed may be a sample obtained from any biological source including, for example, milk, saliva, blood, plasma, lymph, cerebro-spinal fluid, chime, bile, urine, feces, mucus, menses, perspiration, tears, semen, egg, any tissue, bone, a biopsy, tumor, cyst, a sample of a food, beverage, medicine, a lysate/extract or spent media of any biological/culture sample, and the like.

The analyte 22 to be detected can be any material or part thereof including, for example, proteins, peptides, antigens, antibodies, lectins, lectin-binding carbohydrates, tumor markers, disease markers, cytokines, cytokine receptors, hormones, hormone receptors, cell adhesion molecules, cell adhesion molecule ligands, nucleic acids, sugar chains, lipids, a cell, a virus, an intracellular organelle, a small molecule, a low molecular weight compound, and the like. In some embodiments, the sample containing the analyte is pretreated to remove contaminants that can interfere with the assay prior to mixing and detection by the molecular biosensors. For example, treatment options include centrifugation, filtration, gel electrophoresis, column chromatography, DNA precipitation, crude protein precipitation, and the like. In other embodiments, the sample containing the analyte is not pre-treated prior to mixing and detection by the molecular biosensors.

In some embodiments, the biosensor and/or system is directed to detection of a disease marker such as, for example, a tumor marker. A tumor marker can be a characteristic antigen that is differentially expressed on or in association with a neoplastic disease or other tumor type. Likewise, a disease marker can be any detectable analyte associated with any disease. Accordingly, a disease marker can be, for example: a protein; an antibody; a receptor or receptor ligand; an extracellular matrix molecule, fragment or component; a glycan or other carbohydrate; a cell-wall fragment; and the like, wherein such analytes correlate with presence of a disease such as, for example, diseases caused by neoplastic growth, viral infections, bacterial or fungal infections, parasites, autoimmune diseases, prion diseases, and the like.

The affinity moiety 16 can be, for example, an antibody, diabody, minibody (Presta 2003, herein corporated by reference in its entirety), antibody-derived single chain Fv, helix-stabilized Fv, Fv, a part of Fv, $F(ab')_2$, Fab, mutants thereof, and the like, each thereof recognizing different sites in the analyte.

The reporter component 14 can be any material that is a fluorescent material, an enzyme, an enzyme fragment, an enzyme subunit, a receptor, a ligand, a fluorescent protein, a luminescent protein, a non-protein fluorophore, a non-protein chemiluminescent compound, a fluorophore-labeled protein, a fluorescent nanocrystal, a fluorescent chelate, a photosensitizer dye, a fluorescence quencher, and the like.

In one embodiment, the reporter component contains a fluorescent material that participates in a fluorescent resonance energy transfer (FRET) interaction that produces a signal when an analyte is detected. The FRET interaction manifests itself as a detectable signal, which includes, for example, generation of signal above background, alteration of signal emission, alteration of signal magnitude, alteration of signal frequency, alteration of signal wavelength, quenching of signal, and the like. The detectable signal can be produced by FRET pairs such as, for example, fluorescein isothiocyanate (FITC) and tetramethylrhodamine isothiocynanate (TRITC); Alexa 488 and Cy3; Cy3 and Cy5; Blue Fluorescent Protein (BFP) and Green Fluorescent Protein (GFP); BFP and Yellow Fluoiescent Protein (YFP); Cyan Fluorescent Protein (CFP) and YFP; and CFP and dsred [U.S. patent application Ser. No. 11/083,461, published as US 2006/0068502 A1, herein incorporated by reference in its entirety.] Other useful embodiments include the use of FRET cooperative components such as, for example, "LANCE" europium chelate and an allophycocyanin (APC) or Cy5 fluorophore, which are useful for time-resolved (TR)-FRET and generally provide a higher assay sensitivity [Zhang et al. 2005, herein incorporated by reference in its entirety]. Reporter components involving "relay" FRET components, such as fluorescently-emitting quantum dots (QDs), fluorophores, fluorescent proteins, and the like [Medintz et al. 2003, Clamme and Deniz 2005, each of the foregoing which is herein incorporated by reference in its entirety] are also useful embodiments of the present invention. An example involving relay FRET is presented in FIG. 5.

Figure 6:
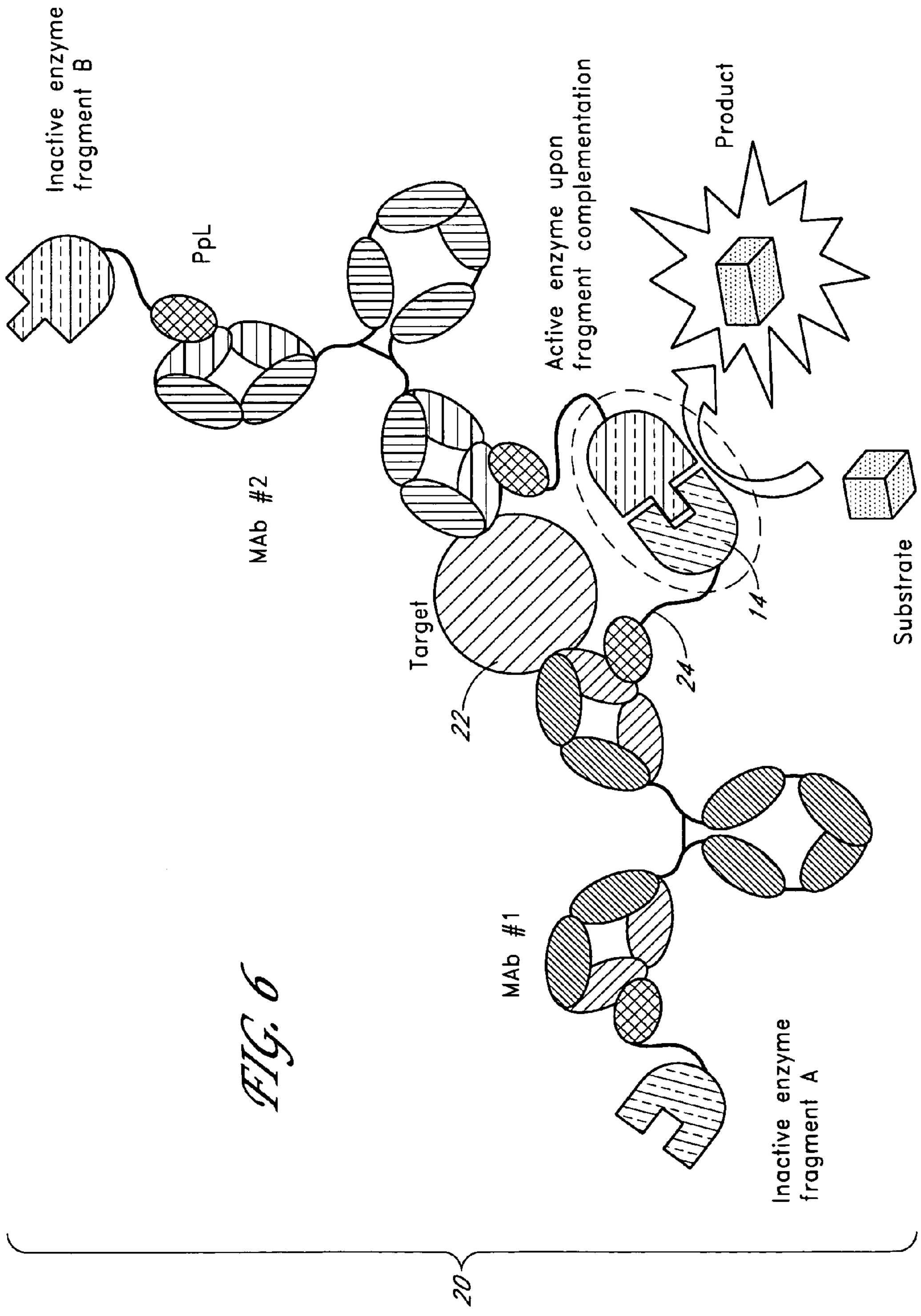
FIG. 6 shows a cooperative reporter system in which the reporter components of the molecular biosensors are enzyme fragments that interact and reconstitute enzymatic activity to produce a detectable signal in the presence of a target analyte, exemplified by formation of a detectable product.

Alternative to FRET, embodiments of the present invention can employ protein or enzyme fragment complementation for signaling as shown in FIG. 6. One enzyme fragment is bound via a PpL domain to a monoclonal antibody specific for the analyte to be detected, the other to a second monoclonal antibody that recognizes different epitopes of the same analyte. Upon binding to the target analyte by both antibodies, the enzyme fragments will recombine to generate a detectable signal by catalytic conversion of various substrates. The enzymatic activity can catalyze a reaction that results in a detectable signal that is bioluminescent, chemiluminescent, fluorescent, and the like. The signal can also result from a change or formation of detectable properties in the enzymatic reaction products. Examples of enzyme complementation systems include beta-galactosidase, beta-lactamase, luciferase, ubiquitin, and murine dihydrofolate reductase (mDHFR) (Deo 2004, herein incorporated by reference in its entirety). In one embodiment, the enzyme fragment or subunit is tethered to the biosensor by a flexible or rigid connecting element of suitable length. The connecting element can be composed of peptides, nucleic acids, sugar chains, proteins, complexes thereof, and the like. In another embodiment, the enzyme fragment or subunit is tethered directly to the biosensor by chemical linkages. Embodiments of the present invention can also use fluorescent protein fragment complementation in the reporter component, in which a fluorescent signal will emerge upon reassembly of the fluorescent protein fragments when they come in close proximity of each other. Examples of fluorescent protein fragment complementation include split green fluorescent protein and yellow fluorescent protein.

In a third embodiment, the reporter component contains a receptor or ligand that participates in a receptor-ligand interaction when an analyte is present. Detection of the analyte can be accomplished by interaction of the reporter with the analyte that produces a detactable signal. The detectable signal can manifest itself as a change in phase, precipitation of solids, change in color or optical property of the sample, and the like.

In a preferred embodiment of the invention, the adapter molecule includes a Protein L-based linker that includes Protein L or fragment or derivative thereof. Protein L can be modified to introduce elements that allow linking to a reporter component. In one embodiment, an A20C mutation is introduced into the Protein L B1 domain at one of two antibody binding sites such that a cysteine residue is introduced into the amino acid sequence (SEQ ID NO: 6). In other embodiments, a T30C mutation is introduced into Protein L B1 domain (SEQ ID NO: 7). The mutation reduces antibody binding at the specific site while simultaneously allowing modification of the site to allow self-assembly of Protein L with at least one reporter component. In a preferred embodiment, the self-assembly involves biotin-streptavidin conjugation in which the streptavidin molecules, for example, can be easily labeled with multiple chemical fluorophores to become an effective reporter. In other embodiments, the self-assembly can involve site-specific chemical coupling (e.g. via thiol-reactive conjugation), protein-protein interactions, weak chemical interactions, and the like.

Figure 7:
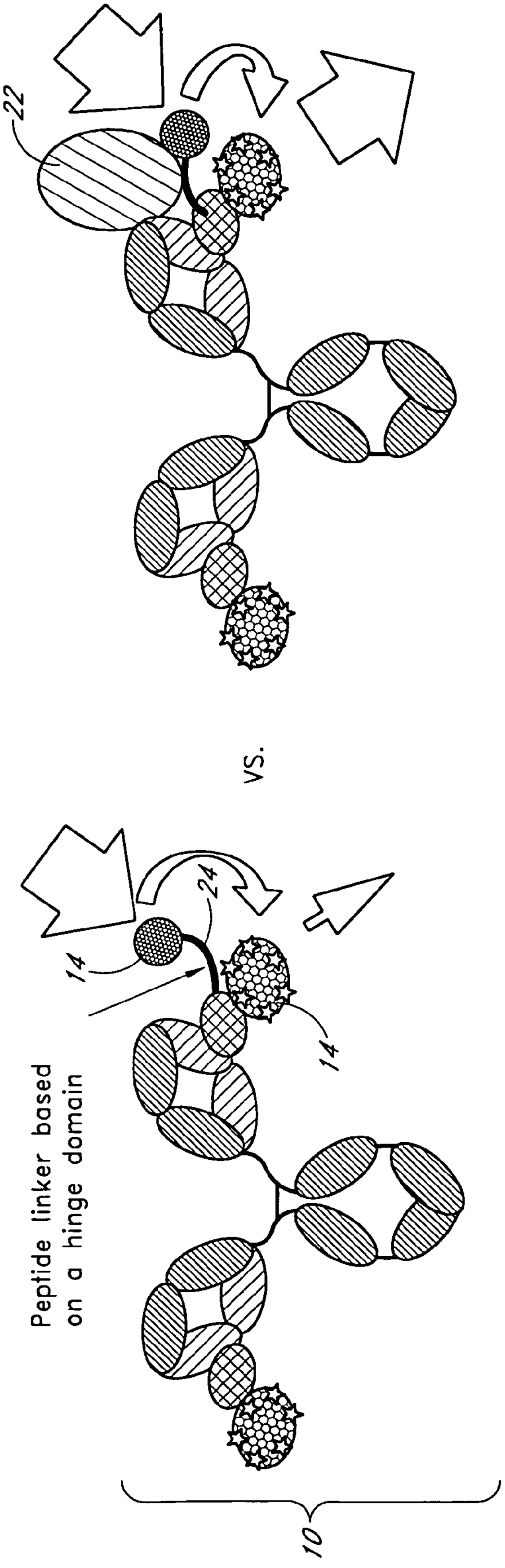
FIG. 7 depicts a molecular biosensor that contains two cooperative reporter components wherein binding of an analyte leads to a detectable signal, exemplified by an alteration in the intramolecular FRET signal interaction.

Reporter components can also be linked to Protein L via additional connecting elements. For example, a fluorescent protein or enzyme fragment can be covalently linked to PpL via genetic fusion (FIG. 1). The PpL molecule can also be labeled directly with chemical fluorophores (FIG. 1). A peptide tag containing suitable reactive amino acid residues (e.g. lysine or cysteine) can be fused with PpL via genetic fusion to enhance the extent of reporter labeling of PpL (FIG. 1). In addition, one can fuse a peptide linker 24 having hinge-bending property (e.g. many proteins, including antibodies, contain hinge regions) to the N- or C-terminus of PpL and introduce a FRET donor or accepter at the end of the linker. Upon binding to an antigen target, the antigen can push the FRET label on the linker closer or away from the counter FRET label linked to the other terminus of PpL or conjugated to one of the binding sites, and cause a change in FRET (FIG. 7). In one embodiment, the additional connecting element is a peptide fused to the C-terminus of Protein L. In another embodiment, the connecting element is a peptide fused to the N-terminus of Protein L. In other embodiments, the connecting element can be composed of materials such as, for example, nucleic acids, sugar chains, proteins, complexes thereof, and the like that are attached to Protein L at one end and to reporter molecules at the other end of the linker.

Protein L can also be modified to introduce elements that allow linking to an affinity moiety. For example, an unnatural amino acid residue can be introduced into the Protein L B1 domain near its antibody (Ig)-binding site. In a preferred embodiment, the unnatural amino acid residue is p-benzoyl-L-phenylalanine (Bpa). Bpa is introduced in vivo into Protein L using an engineered orthogonal aminoacyl-tRNA synthetase/tRNA pair with an *Escherichia coli* (*E. coli*) protein expression host. In one embodiment, the T39 site in the Protein L B1 domain is targeted for mutation. In another embodiment, the K41 site in the Protein L B1 domain is targeted for mutation. The mutated Protein L can self-assemble with the affinity moiety. In a preferred embodiment, the Protein L-affinity moiety complex can be covalently linked by exposing it to long-wavelength UV light (about 360 nm) in order to photocrosslink the complex. (See FIG. 2.)

Protein L can be modified to allow linking of both an affinity moiety and at least one reporter component.

Figure 5:
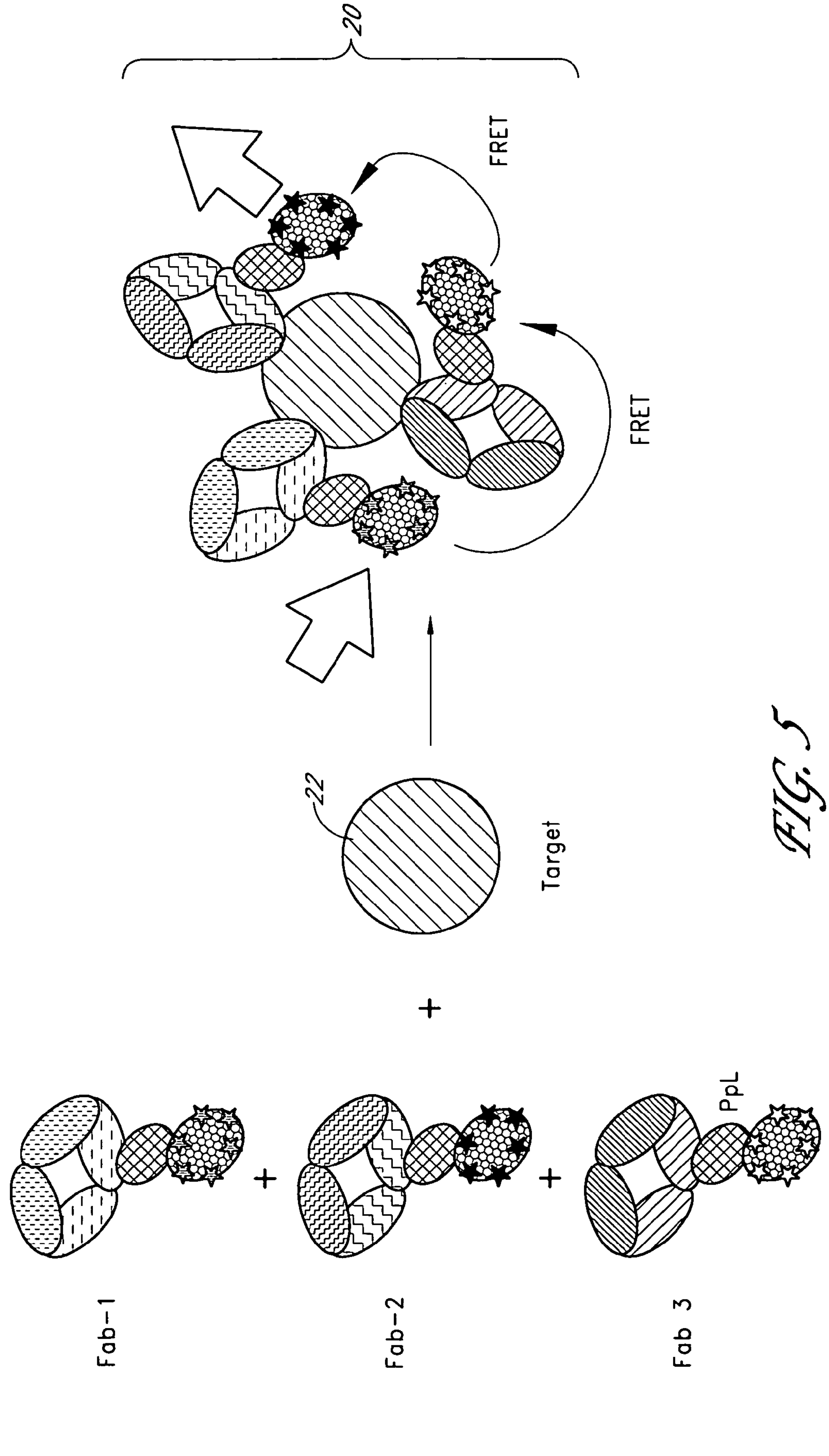
FIG. 5 illustrates a homogeneous non-competitive immunoassay using a cooperative reporter system based on multiple molecular biosensors, each containing a reporter-Protein L-antibody fragment complex whose reporter components participate in relayed FRET.

The molecular biosensor has at least one cooperative reporter component tethered to it. In one embodiment, the molecular biosensor has only one cooperative reporter component linked to it. In the presence of an analyte, the biosensors are brought into close proximity by binding the analyte such that the first reporter in the first biosensor interacts with at least a second reporter in a second biosensor to produce a detectable signal. (See FIGS. 3 and 4.) In one embodiment, the first reporter in the first biosensor interacts with a second reporter in the second biosensor to produce a detectable signal. In another embodiment, the first reporter in the first biosensor interacts with a second and a third reporter component from a second and a third biosensor, respectively, to produce a detectable signal. The interaction between the three reporters can be simultaneous. Alternatively, it can involve a "relay" interaction where the first reporter interacts with the second reporter, which subsequently interacts with the third reporter to produce a detectable signal, as depicted in FIG. 5 [Medintz et al. 2003, Watrob et al. 2003, Galperin et al. 2004, each of the foregoing which is herein incorporated by reference in its entirety]. In another embodiment, the first reporter in the first biosensor interacts with three or more other reporter components, each individually linked to different biosensors, in order to produce a detectable signal. The interaction between the four or more components can occur simultaneously, or it can involve a "relay" interaction between the reporter components.

Figure 10:
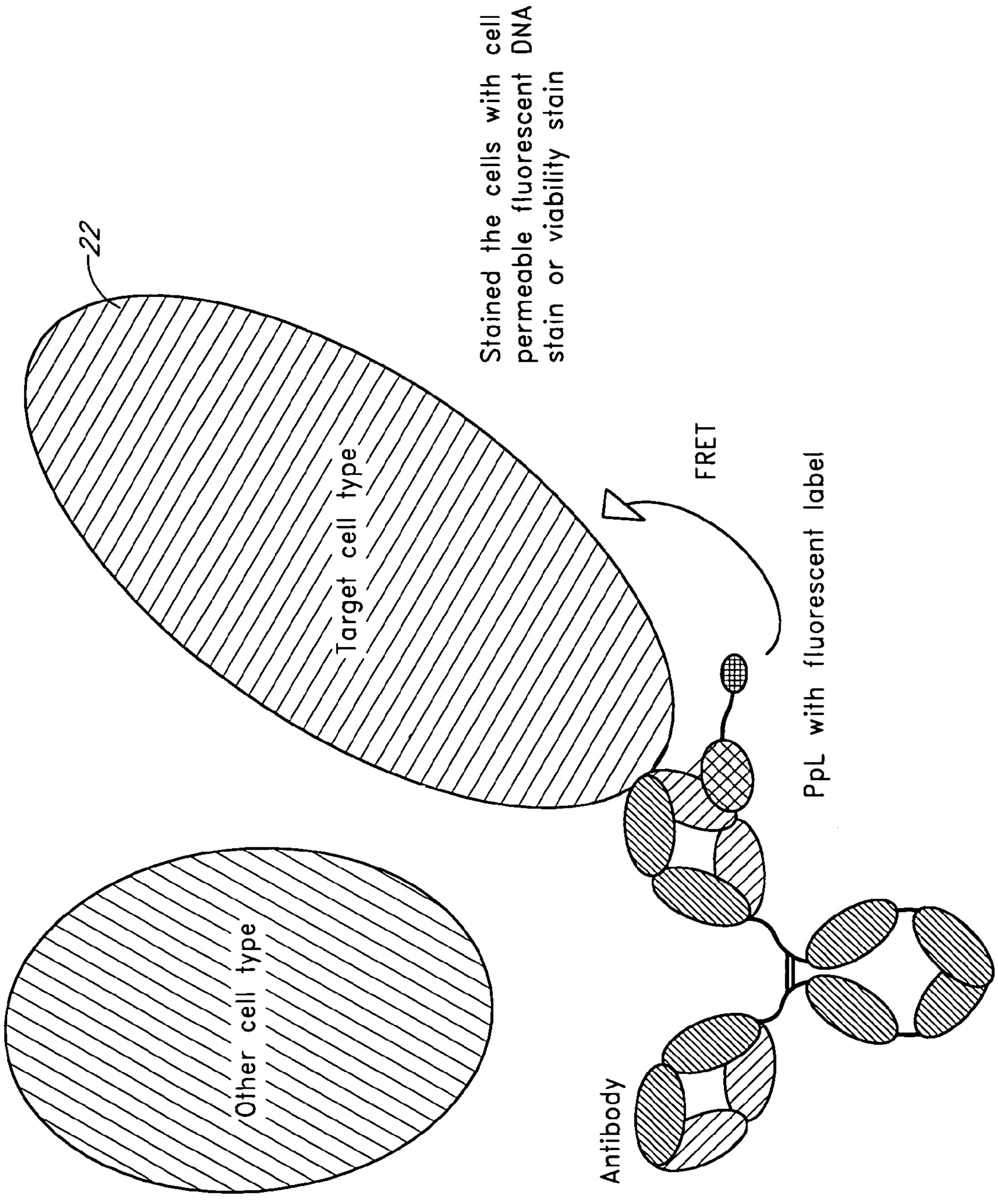
FIG. 10 depicts a molecular biosensor interacting with a fluorescently stained target cell to generate a detectable signal. The cell which is not stained or does not interact with the biosensor does not produce any detectable signal.
Figure 11:
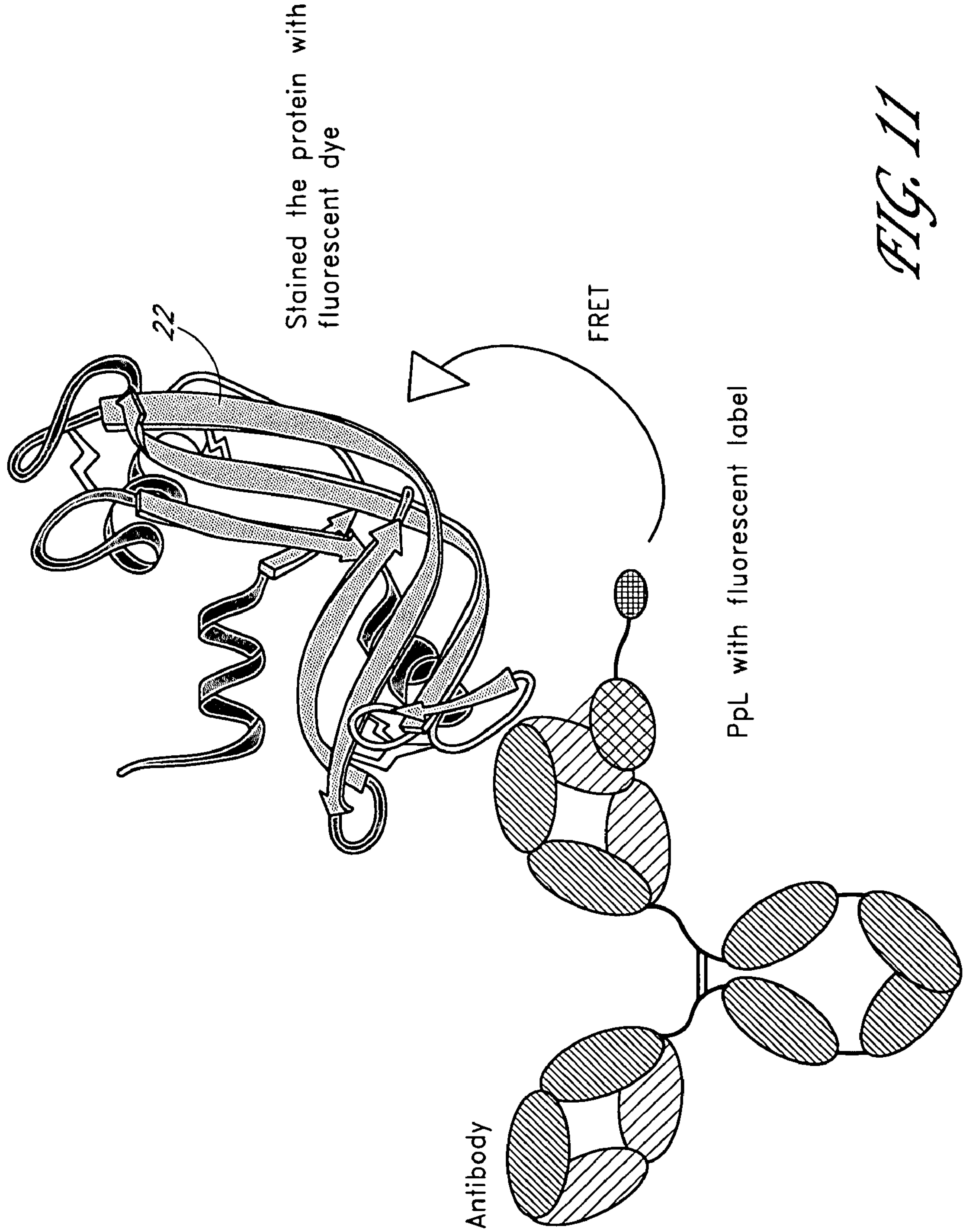
FIG. 11 shows a molecular biosensor interacting with a fluorescently stained protein to generate a detectable signal.

In other embodiments, the analyte can act as a cooperative reporter entity to interact with the biosensor reporter component to produce a detectable signal. (See FIGS. 10 and 11.) For example, the analyte can include a cell stained with a fluorescent dye, a protein stained with a fluorescent dye, a biological material stained with a fluorescent dye, and the like.

Figure 8:
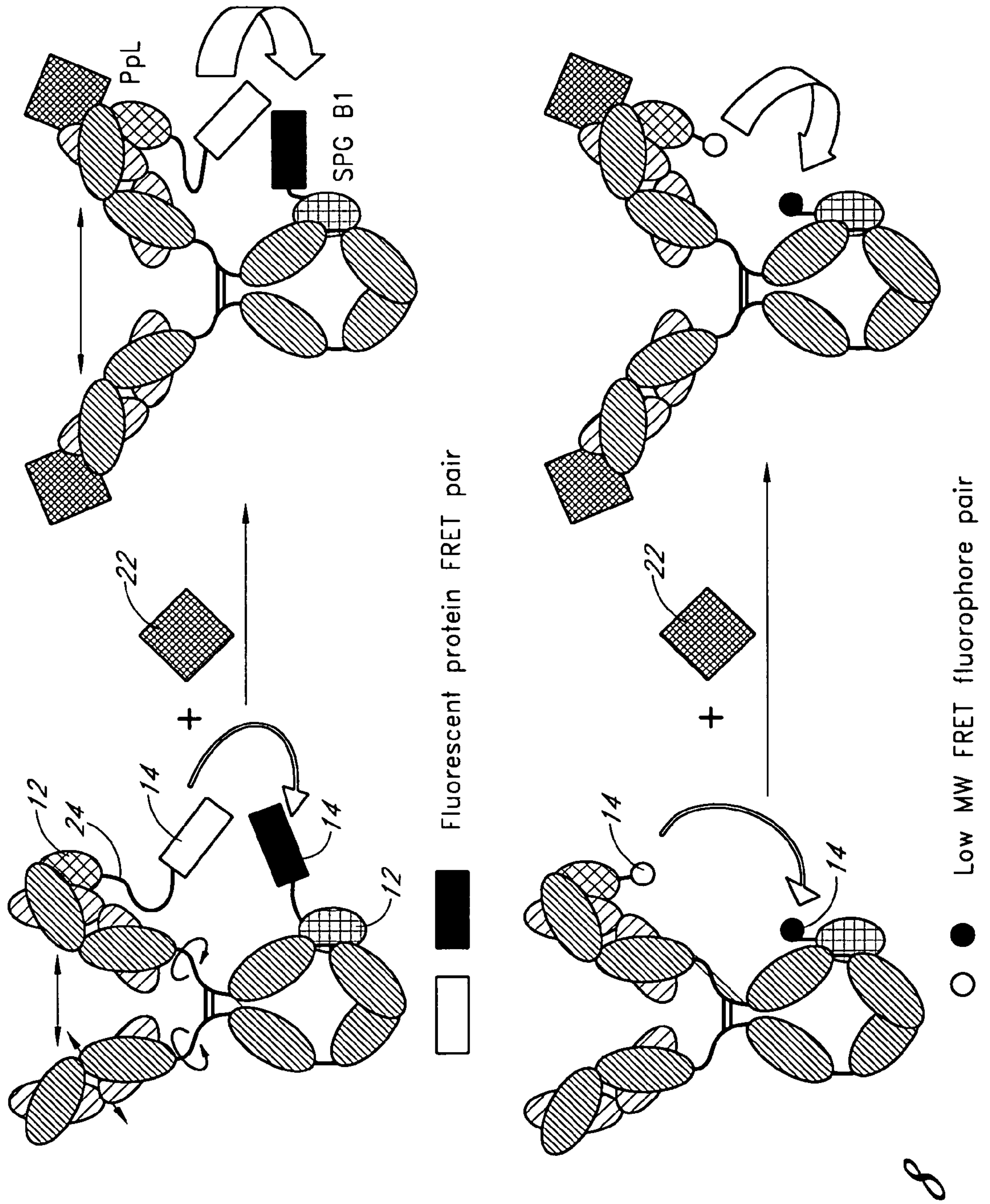
FIG. 8 shows a molecular biosensor complexed with a PpL molecule tethered to a first reporter component and additionally complexed to a Protein G molecule tethered to a second reporter component. Interaction of the reporter components leads to generation of a detectable signal, or a detectable change in signal, when an analyte binds to the biosensor.
Figure 12:
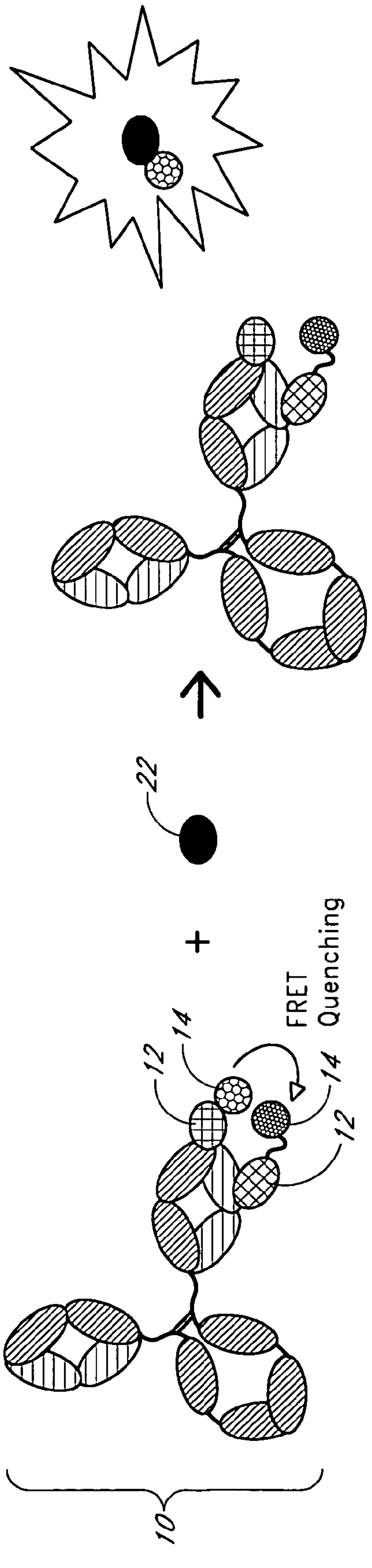
FIG. 12 illustrates a molecular biosensor with two cooperative reporter components that quench each other's signal activity in the absence of an analyte. The presence of an analyte interacts with one of the reporter components such that it removes the component from the biosensor, allowing restoration of a detectable signal.

Embodiments of the invention can employ molecular biosensors that contain at least two cooperative reporter components in a cooperative reporter system 20, which interact with each other and produce a detectable signal in the presence of an analyte. In one embodiment, the biosensor contains two reporter components that quench each other such that no signal is detected in the absence of an analyte. In the presence of an analyte, the analyte interacts with the biosensor such that the reporter components become separated and a detectable signal is generated due to restoration of signal emission. Fluorescent materials such as, for example, EDANS (5-(2'-aminoethyl)aminonapthalene-1-sulfonic acid), fluorescein, and rhodamine are quenched by DABCYL (4-(4'-dimethylaminophenylazo) benzoic acid) [Vet et al. 1999, herein incorporated by reference in its entirety]. The removal of quencher from close proximity to the fluorescent materials restores detectable signal emission (FIG. 12). Additional FRET quenching materials, such as those considered in U.S. patent Ser. No. 11/083,461 (published as U.S. 2006/0068502 B1), are also suitable in embodiments of the present invention. In another embodiment, the two reporter components produce a baseline signal in the absence of an analyte. When an analyte is present, it interacts with the biosensor such that the interaction between the two reporters is altered due to a conformational change in the hinge region of the antibody molecule, resulting in a detectable signal that is manifested as a change in signal relative to the baseline emission [Lichlyter et al. 2003, herein incorporated by reference in its entirety]. (See FIGS. 8 and 9.) In a third embodiment, the two reporter components do not interact in the absence of an analyte. When an analyte is introduced into the sample, it interacts with the biosensor such that the two reporter components are brought into close proximity, producing a detectable signal above baseline. For example, the detectable signal can be produced by a FRET pairs such as those described in U.S. patent Ser. No. 11/083,461 (published as U.S. 2006/0068502 B1). Embodiments of the present invention can employ molecular biosensors that contain three or more cooperative reporter components, which interact with each other and produce a detectable signal in the presence of an analyte. The reporter components can interact simultaneously with each other, or they can interact in a "relay" matter in which the first reporter interacts with the second reporter, which subsequently interacts with the third reporter, and so on until the last interaction takes place. In the presence of an analyte, the biosensor can bind the analyte such that a detectable signal is generated from interaction of the intramolecular reporter components. The detectable signal can involve signal quenching, signal interference, signal generation, signal alteration, and the like.

Figure 9:
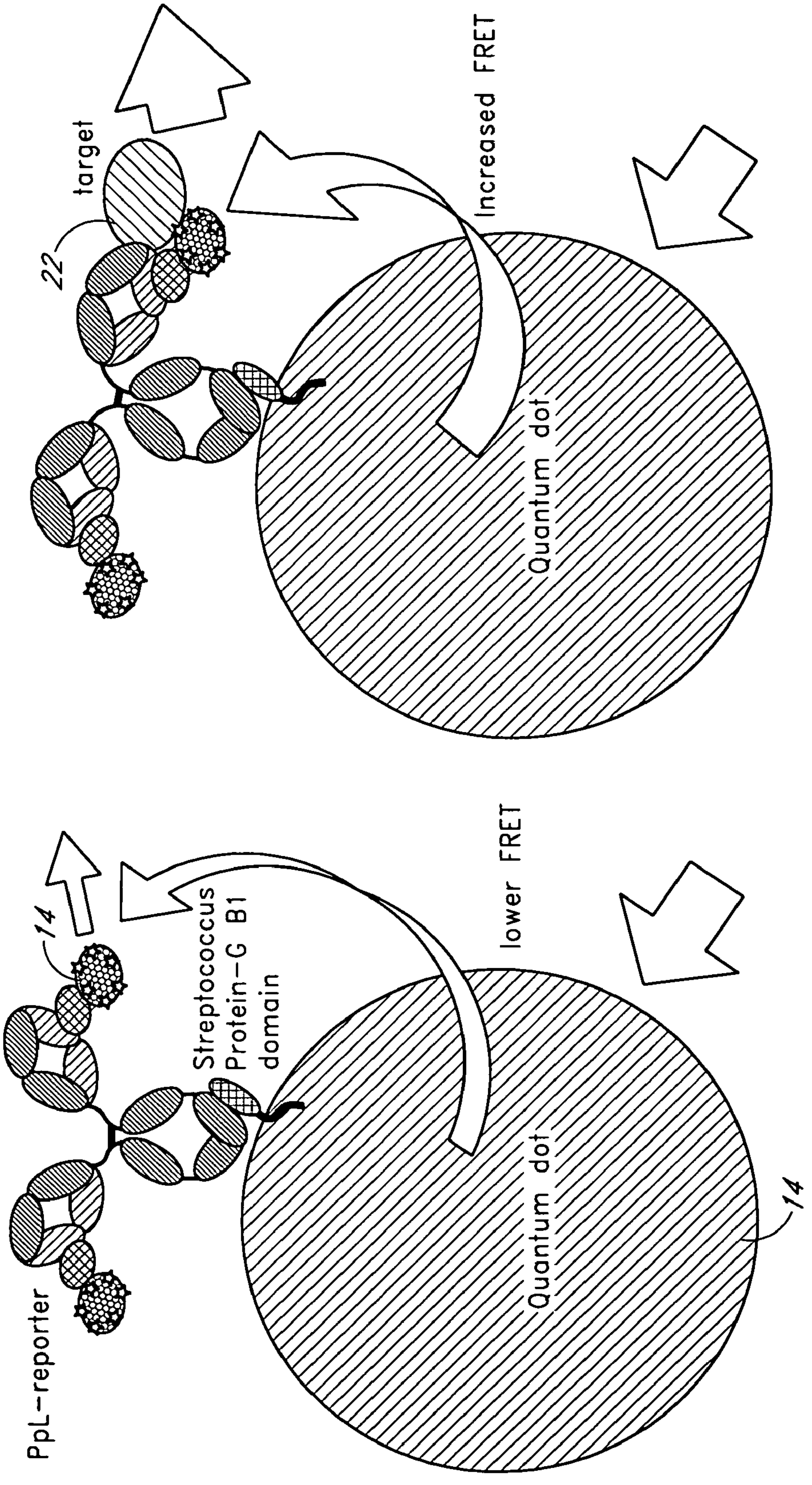
FIG. 9 illustrates a a molecular biosensor complexed with a PpL molecule tethered to a first reporter component and additionally complexed to a Protein G molecule tethered to a second reporter component that is a quantum dot. Interaction of the first reporter with the quantum dot leads to generation of a detectable signal, or a detectable change in signal, when an analyte binds to the biosensor.

In some embodiments, the affinity moiety is linked to at least one reporter component via Protein L; in addition, the affinity moiety can be linked to at least one other reporter component via other antibody binding proteins such as Proteins A, G, H, and M. (See FIGS. 8 and 9.) The reporter components can interact with each other and produce a detectable signal upon binding to a target analyte. This is based on the fact that antibodies undergo conformational changes in the hinge region upon binding to antigens, which produce a detectable signal [Lichlyter et al. 2003, herein incorporated by reference in its entirety]. The detectable signal can manifest itself as a FRET interaction which includes generation of signal above background, alteration of signal emission, alteration of signal magnitude, alteration of signal frequency, alteration of signal wavelength, quenching of signal, signal interference, and the like; as an enzymatic reaction that produces a detectable signal that is bioluminescent, chemiluminescent, fluorescent, results in changes in the spectral properties of the sample, and the like; or as a change in phase, precipitation of solids, change in color or optical property of the sample, and the like. (See FIGS. 8 and 9.) As illustrated in FIG. 9, antibody molecules can be captured by a Fc-binding Streptococcus Protein-G B1 domain immobilized on a quantum dot [Medintz et al. 2003, herein incorporated by reference in its entirety] which serves as either a FRET donor or acceptor, while the PpL adapter is coupled to a reporter group that forms a FRET pair with the quantum dot. On binding to a target, the self-assembled, self-signaling antibody can display an altered FRET activity due to conformational changes in the hinge region of the antibody.

In some embodiments, detection of the signal generated by presence of the analyte requires instrumentation such as a fluorometer, luminometer, spectrophotomer, plate reader, and the like. In other embodiments, detection of the signal does not require instrumentation and is visible to the naked eye.

Methods and materials known in the art and generally relevant to biosensor and immunoassay technology such as those used in the present invention are described in U.S. Pat. No. 5,981,199, U.S. Pat. No. 6,162,903, U.S. Pat. No. 6,884,629 B2, and U.S. patent application Ser. No. 10/475,540 (published as U.S. 2004/0110245 A1), each of the foregoing which is herein incorporated by reference in its entirety.

Table 1 provides a list of nucleotide and amino acid sequences related to the PpL B1 linking components of the present invention.

TABLE 1

| Linking Component | Nucleotide Sequence | Amino Acid Sequence |
|---|---|---|
| PpL B1 domain (Y47W mutation) | SEQ ID NO: 1 | SEQ ID NO: 6 |
| PpL B1 domain (Y47W and A20C mutations) | SEQ ID NO: 2 | SEQ ID NO: 7 |
| PpL B1 domain (Y47W and T30C mutations) | SEQ ID NO: 3 | SEQ ID NO: 8 |
| PpL B1 domain (Y47W and T39Amber mutations) | SEQ ID NO: 4 | SEQ ID NO: 9 |
| PpL B1 domain (Y47W and K41Amber mutations) | SEQ ID NO: 5 | SEQ ID NO: 10 |

EXAMPLES

Example 1

Modification of *Peptostreptococcus* Protein L (PpL) for Site-Specific Coupling with a Reporter Component

Figure 14:
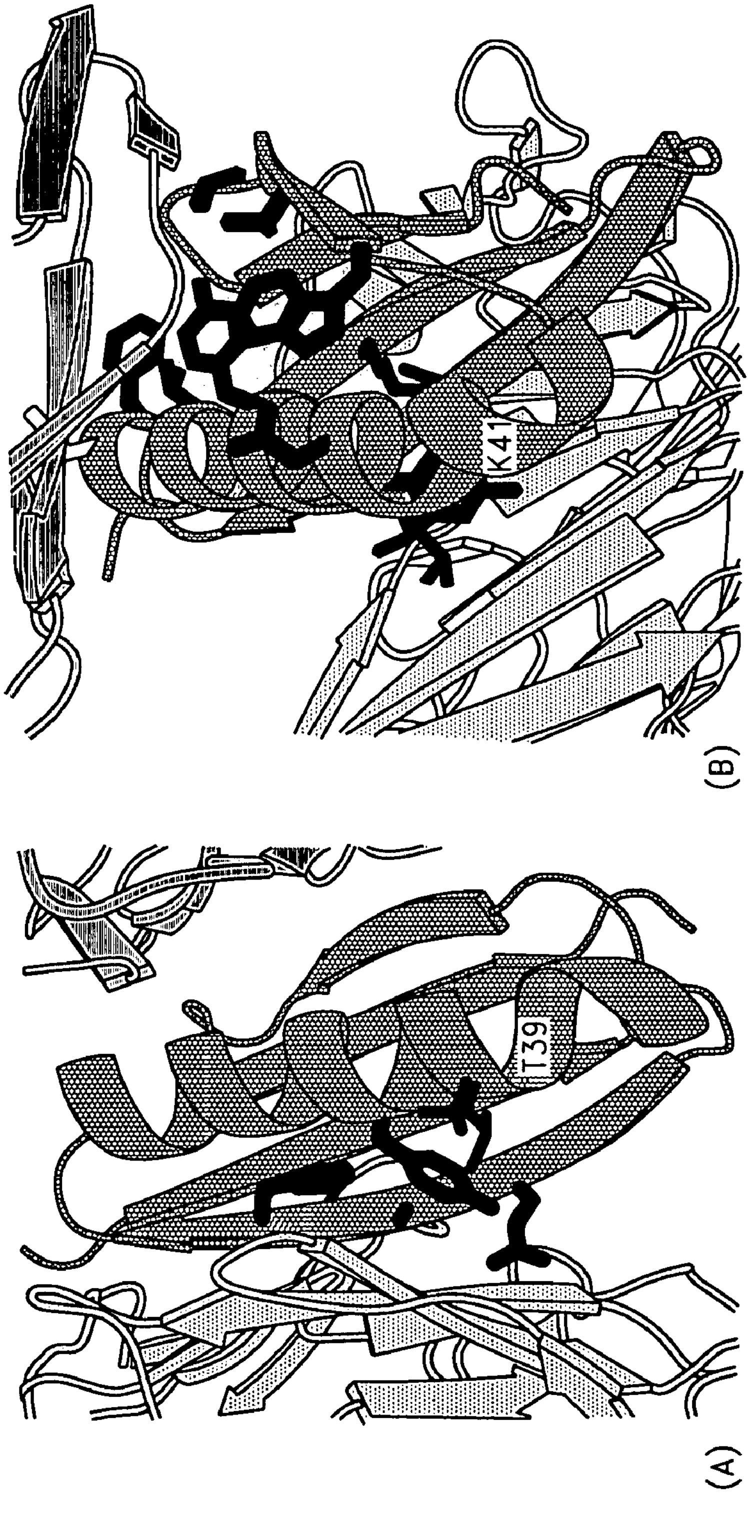
FIG. 14 illustrates binding sites within the Protein L B1 domain.

*Peptostreptococcus magnus* PpL B1 domain has two binding sites for Ig κ light chains corresponding to the two edges of its beta-sheet [Svensson et al. 2004, herein incorporated by reference in its entirety] (FIG. 14). To form a desired 1:1 ratio of PpL/Ig-κ complex (as indicated in FIG. 2), a combination of site-directed mutation and biotin/streptavidin (SA)-mediated protein assembly is used to block site 1 binding to Ig-κ. An A20C mutation is introduced to the PpL B1 domain containing a Y47W mutation (SEQ. ID NO: 1 and 6, supplied by Drs. Ulf Sjöbring and David Baker) by means of a site-directed mutagenesis method such as that described in U.S. Pat. No. 6,713,285 (herein incorporated by reference in its entirety) using mutation primers (forward: 5'-ATCCACACAAACTTGCGAATTCAAAGGAACATTTG-3'; reverse: 5'-TTCCTTTGAATTCGCAAGTTTGTGTGGATCCATTTGC-3') which introduces a single cysteine at the center of site one [Svensson et al. 2004]. The A20C mutation (SEQ ID NO: 2 and 7) allows site-specific labeling of PpL at the center of site one with a thiol-reactive biotin molecule (for example, maleimide $PEO_2$-Biotin (Pierce, Rockford, Ill.), a water-soluble sulfhydryl-reactive biotinylation reagent), which in turn enables coupling with a reporter-labeled streptavidin molecule. Alternatively, the A20C mutant can be labeled with a thiol-reactive fluorescent dye (such as maleimide derivative of fluorophores). The gene encoding the A20C mutant of the PpL B1 domain can be expressed as a histidine-tagged protein using a pET21 vector and purified using an immobilized metal affinity chromatography column. In addition to the A20C mutation, a T30C mutation (SEQ. ID NO: 3 and 8) using mutation primers (forward: 5'-ATTTGAAAAAGCATGCAGTGAAGCTTATGCAGATAC-3'; reverse: 5'-ATAAGCTTCACTGCATGCTTTTTCAAATGTTCC-3') provides an alternative means to disrupt the site 2 binding of PpL [Svensson et al. 2004].

Example 2

Modification of Peptostreptococcus Protein L (PpL) for Covalent Linkage to an Affinity Moiety To enable covalent attachment of the PpL B1 domain to the Ig kappa variable light chain, an unnatural photocrosslinking amino acid residue (p-benzoyl-L-phenylalanine, or Bpa) is introduced into the His-tagged PpL-B1 mutant (Example 1) near its Ig-binding site using an engineered orthogonal aminoacyl-tRNA synthetase/tRNA pair for the in-vivo incorporation of Bpa into proteins in *Escherichia coli* (*E. coli*) in response to the amber codon, TAG [Chin et al. 2002(a), Chin et al. 2002(b), Farrell et al. 2005, each of the foregoing which is incorporated by reference in its entirety]. Within the PpL B1 domain structure near its two binding sites, T39 (labeled pink in FIG. 14A) and K41 (labeled cyan in FIG. 14B) are targets for mutation to Bpa for binding site 1 and 2 respectively. To introduce the Bpa, two plasmids are employed: (1) a p15A-based plasmid (pDULE) to express the orthogonal tRNA and synthetase pair (obtained from Dr. Peter Schultz), and (2) a second plasmid containing an amber mutant of the PpL B1 domain (SEQ ID NO: 4, 5, 9, and 10). *E. coli* is transformed with these two plasmids and grown in the presence of Bpa in the media. The Bpa-incorporated PpL B1 is then purified by standard protein purification techniques (Example 1) prior to incubation with antibodies to link them together.

Example 3

Linking of the Reporter Component to Modified PpL B1 Molecules

The biotinylated His-tagged PpL B1 mutant (Example 1, Example 2) is immobilized on a Ni-NTA column, and fluorophore-labeled streptavidin (SA) is pumped through the column to form a 1:1 complex with the PpL mutant. The protein complexes that form on the column are then eluted by immidazol, dialyzed to remove leached nickel ions and excess immidazol, and subjected to gel filtration chromatography for further purification and analysis to check for their molecular size distribution. Separate pools of PpL B1 domain molecules are individually labeled in this manner to produce a wide variety of adapter molecules for use in assays of the present invention.

Example 4

Covalent Linking of Antibodies to Modified PpL B1 Molecules

The Bpa-incorporated PpL B1 (Example 2) is incubated with anti-GMCSF (granulocyte macrophage colony stimulating factor) monoclonal whole and/or Fab antibodies at room temperature for one hour to allow self-assembly of the antibodies with the modified PpL B1 molecules. An optional cross-linking step can be introduced by exposing the PpL/Ab complex to UV light at 360 nm. PpL B1 molecules that do not bind the antibody are separated from the labeled antibodies by using centrifugal or standard membrane ultrafiltration or gel filtration techniques. Before conducting the immunoassays of GMCSF (the target analyte) using the reporter-PpL-Ab complex, the binding characteristics of the protein complex to the GMCSF are examined using standard ELISA and are compared to the performance with un-labeled anti-GMCSF antibodies. Formation of the reporter-PpL-Ab complex can be further optimized by adjusting parameters such as protein concentration, buffer ionic strength, pH, binding temperature.

Example 5

Synthesis of a PpL-Reporter Fusion Protein

A fluorescent protein (such as the green fluorescent protein and its variants) is linked to the N- or C-terminus of the PpL B1 domain via tandem genetic fusion with or without a peptide linker (FIG. 1). A suitable peptide, e.g. the E/K coiled coil (Lindhout et al. 2004 herein incorporated by reference in its entirety) or the tetracysteine tag (Adams et al. 2002, herein incorporated by reference in its entirety), is also fused to the PpL for convenient site-specific reporter labeling. Standard PCR-based molecular cloning methods are used to create such recombinant molecules.

Example 6

Synthesis of PpL Attached to a Second Reporter via a Hinge-Bending Linker

Standard PCR-based molecular cloning methods are used to introduce a peptide linker with hinge-bending properties [Lichlyter et al. 2003] to the N- or C-terminus of the PpL B1 mutant (Examples 1-4). A FRET donor or accepter is introduced at the terminal end of the linker via genetic fusion or chemical conjugation. Upon binding to an antigen target, the antigen pushes the FRET label on the linker closer or further away from the counter FRET label conjugated to one of the mutated Ig-binding sites (site 1 or site 2), causing an alteration in the FRET signal (FIG. 7).

Example 7

Production of a Molecular Biosensor to Detect Human Granulocyte Macrophage Colony Stimulating Factor (GMCSF)

A Protein L B1 domain fusion protein with a hexa-histidine tag fused to its C-terminus and a lysine-rich K3 $(KEKIAAL)_3$ coil peptide tag fused to its N-terminus was produced in *Escherichia coli* and purified using immobilized metal affinity chromatography (IMAC). One pool of PpL B1 fusion protein was chemically labeled with fluorescein isothiocyanate (FITC), while another pool of PpL B1 fusion protein was labeled with tetramethylrhodamine isothiocyanate (TRITC) using standard chemical labeling protocols. After labeling, the unlabeled fluorophores were separated from the labeled PpL B1 fusion proteins by centrifugal ultrafiltration using a 10 kD cut-off membrane. PpL B1 fusion proteins labeled with FITC and TRITC were then respectively incubated with clone 3209 and clone 6804 mouse monoclonal anti-GMCSF antibodies (R&D Systems, Minneapolis, Minn.), each recognizing a distinct epitope on GMCSF antigen, to form self-assembled reporter-linker-antibody complexes. The molar ratio between fluorophore-labeled PpL B1 and antibody was optimized to be greater than 2:1 to maximize the probability that each antibody molecule received two PpL B1 molecules. Subsequently, PpL B1 molecules that did not bind to the antibody were separated from the labeled antibodies by centrifugal ultrafiltration using a 100 kD cut-off membrane (note that PpL is much smaller than an antibody molecule).

Example 8

Figure 13:
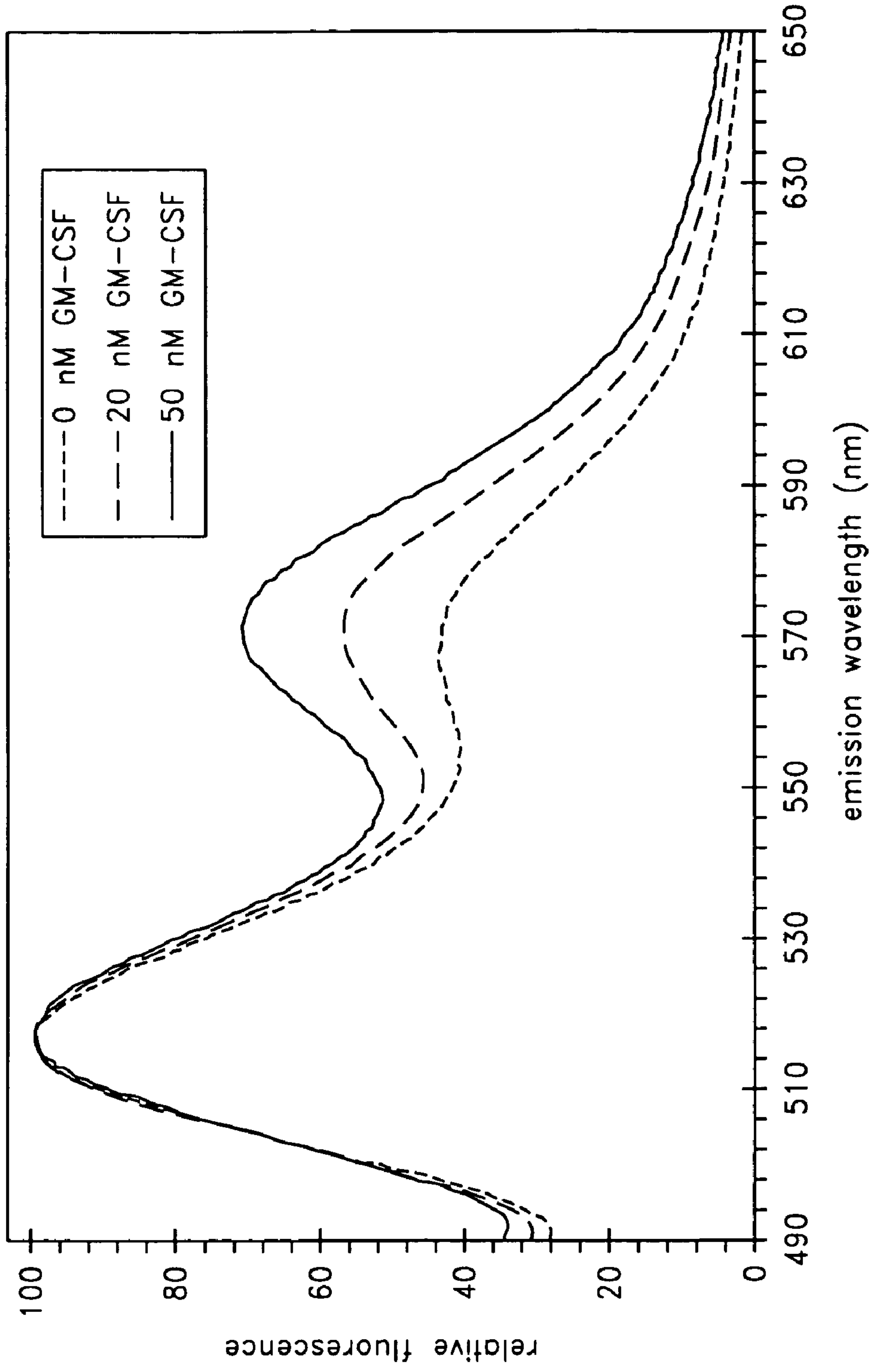
FIG. 13 shows the results of a non-competitive immunoassay involving the cooperative reporter system of the present invention. The presence of a target analyte (GMCSF) results in a detectable signal, exemplified by the alteration in relative fluorescence emission.

Detection of Human Granulocyte Macrophage Colony Stimulating Factor (GMCSF in a Homogeneous Noncompetitive Assay The molecular biosensor complexes (Example 7) were incubated with liquid samples containing GMCSF at three different concentrations [0, 20, 50 nM] for a period of 30 minutes at room temperature. Afterwards, fluorescence spectra of the liquid sample were collected and the degree of FRET was estimated using standard FRET analysis techniques. The FRET signal increased (as indicated by the increasing peak intensity at 580 nm) according to increasing concentrations of GMCSF in the sample (FIG. 13).

Example 9

Preparation of a Biological Sample for Detection of an Analyte

A biological sample is obtained from a specimen, and diluted in a cold buffered solution containing Tris salt at a concentration that ranges from 50 mM to 1M, at pH values ranging from 7.5 to 8.0. Detergents, such as Tween 80 or Triton X-100, is optionally added to the mixture to a final concentration of between 0.1% to 4% v/v. Solids are optionally cleared from the mixture by performing centrifugation at 4° C. at 1000×g for 5 minutes. The cleared supernatant is decanted and reserved for the immunoassay procedure.

Example 10

Demonstration of Reporter-PpL-Affinity Moiety Complexes in a FRET-based Homogeneous Noncompetitive Immunoassay Detection of a GMCSF is carried out using a pair of molecular biosensors containing anti-GMCSF monoclonal whole and/or Fab antibodies complexed to PpL that is attached to either fluorescein isothiocyanate (FITC) or tetramethylrhodamine isothiocyanate (TRITC). In 1.5-mL Eppendorf tube, GMCSF at concentrations ranging from 0 to 200 nM is mixed with solution containing the two fluorophore-labeled molecular biosensors. The mixtures are allowed to incubate from 30 minutes to one hour, at temperatures ranging from 4° C. to room temperature, while shielded from light. After the incubation period, each sample is injected into the cell of a spectrofluorometer, the fluorescence spectra are collected, and the degree of FRET is estimated.

Alternatively, time-resolved (TR)-FRET can be performed on the sample using a different FRET-pair. For example, fluorophores such as europium chelate and an allophycocyanin (APC)/Cy5 are used in (TR)-FRET, which generally provides a higher degree of assay sensitivity [Zhang et al. 2005, herein incorporated by reference in its entirety].

Example 11

Demonstration of Reporter-PpL-Affinity Moiety Complexes in a Split-Enzyme-Based Homogeneous, Noncompetitive Immunoassay Detection of a model analyte, GMCSF, is carried out using a pair of molecular biosensors containing anti-GMCSF monoclonal whole and/or Fab antibodies complexed to PpL that is attached to the $\Delta\alpha$ fragment of $\beta$-lactamase or to $\Delta\omega$ fragment of $\beta$-lactamase. The enzyme fragment is attached to PpL via tandem genetic fusion with a suitable peptide linker using standard PCR-based molecular cloning methods to create such recombinant molecules. In a microfuge tube, a liquid sample containing GMCSF at concentrations ranging from 0 to 200 nM is mixed with solution containing the two enzyme fragment-labeled molecular biosensors. CCF2/AM fluorogenic substrate is also added to the mixture at a final concentration of 2 μM in DMEM. The mixtures are allowed to stand for from 30 minutes to one hour at room temperature. After the incubation period, the change in the ratio of blue-to-green fluorescence emissions of the sample is examined by eye or a fluorometer to determine the presence and concentration of GMCSF.

Example 12

Demonstration of Reporter-PpL-Affinity Moiety Complexes to Detect Fluorescently-Stained Biological Material in a FRET-Based Homogeneous, Noncompetitive Immunoassay Detection of plant pathogenic bacteria *Ralstonia solanacearum* in a liquid sample containing a mixed microbial population is demonstrated using a FITC-labeled molecular biosensor. The microbial culture sample is loaded with the CC1 fluorogenic substrate, which is a substrate for beta lactamase, an enzyme that is found universally in bacteria. The CC1 product can be excited at 550 nm to emit a red fluorescent signal at 585 nm [Gao et al 2003, herein incorporated by reference in its entirety]. The CC1 substrate is used here to stain the microbial cells. The presence of pathogen in the sample is determined by binding between the CC1-loaded *R. solanacearum* and the molecular biosensor, which contains a FITC-labeled PpL adapter coupled to the *R. solanacearum* specific antibody. Binding of the molecular biosensor to the substrate-loaded pathogen elicits a signal produced by the FRET interaction between the FITC reporter and the CC1 product.

Example 13

Demonstration of Multi-Component Reporter-PpL-Affinity Moiety Complexes that Self-Assemble to Detect Analytes in a FRET Interference-based Homogeneous Noncompetitive Immunoassay Fab fragments are derived from three distinct clones of anti-streptavidin monoclonal antibodies, each recognizing a different epitope on an the antigen. The Fab fragments are used to create three PpL-based molecular biosensors. The reporter components in the PpL-based biosensors are chosen to enable relay FRET, e.g. Alexa488/TMR/Cy5. Preparation of the complexes is as described in Examples 1-4. In an assay to determine the presence of antigen, the three molecular biosensors are incubated with a liquid sample containing streptavidin at concentrations ranging from 0 to 200 nM for an hour at room temperature while shielded from light. After the incubation period, each sample measured in a fluorometer, and the fluorescence spectra are collected. In the presence of streptavidin, relay FRET occurs, generating an alteration in the fluorescence emission spectra of the sample.

REFERENCES

Adams, S. R. et al. 2002. New biarsenical ligands and tetracysteine motifs for protein labeling in vitro and in vivo: synthesis and biological applications. *J Am Chem Soc.* 124(21):6063-76.

Chin, J. W. et al. 2002(a). *Proc Natl Acad Sci USA* 99:11020-11024.

Chin, J. W. and P. G. Schultz. 2002(b). *Chembiochem* 3:1135-1137.

Clamme, J.-P. and Ashok A. Deniz. 2005. Three-Color Single-Molecule Fluorescence Resonance Energy Transfer. *ChemPhysChem* 6: 74-77.

De Chateau, M. et al. 1993. *Scand J Immunol* 37:399-405.

Deo, S. K. 2004. Exploring bioanalytical applications of assisted protein reassembly. *Anal Bioanal Chem* 379: 383-390.

Farrell, I. S. et al. 2005. *Nat Methods* 2:377-384.

Galarneau, A. et al. 2002. *Nat Biotechnol* 20:619-622.

Galperin, E. et al. 2004. Three-chromophore FRET microscopy to analyze multiprotein interactions in living cells. *Nature Methods* 1(3): 209-217.

Gao, W. et al. 2003. Novel Fluorogenic Substrates for Imaging beta-Lactamase Gene Expression. *J. Am. Chem. Soc.* 125(37):11146-11147.

Kastem, W. et al. 1992. Structure of peptostreptococcal protein L and identification of a repeated immunoglobulin light chain-binding domain. *J. Biol. Chem.* 267, 12820-5.

Komiya, N. et al. 2004. *Anal Biochem* 327:241-246.

Lichlyter, D. J et al. 2003. *Biosens Bioelectron* 19:219-226.

Lindhout, D. A. et al. 2004. NMR solution structure of a highly stable de novo heterodimeric coiled-coil. *Biopolymers* 75(5):367-75

Medintz, I. L. et al. 2003. *Nat Mater* 2:630-638.

Ohiro, Y. et al. 2002. *Anal Chem* 74:5786-5792.

Presta, L. 2003. Antibody engineering for therapeutics. *Current Opinion in Structural Biology* 2003, 13:519-525.

Renard, M. et al. 2002. *J Mol Biol* 318:429-442.

Renard, M. and H. Bedouelle, 2004. *Biochemistry* 43:15453-15462.

Selvin, P. R. 1995. *Methods Enzymol* 246:300-334.

Svensson, H. G. et al. 2004. *Biochemistry* 43:2445-2457.

Ueda, H. et al. 1999. *Biotechniques* 27:738-742.

Ueda, H. et al. 2003. *J Immunol Methods* 279:209-218.

Ueda, H., et al. 2004. *Biotechniques* 290:107-120.

Vet et al. 1999. Multiplex detection of fourpathogenic retroviruses using molecular beacons. *PNAS* 96(11):6394-6399.

Watrob, H. M. et al. 2003. Two-Step FRET as a Structural Tool. *J. Am. Chem. Soc.* 125:7336-7343.

Wehrman, T. et al. 2002. *Proc Natl Acad Sci U S A* 99:3469-3474.

Yang, X. et al. 2005. *Anal Biochem* 336:102-107.

Zhang, W. X. et al. 2005. *Anal Biohem* 343:76-83.

---

What is claimed is:

1. A method of sensing an analyte, comprising the steps of providing a biological sample;

contacting the sample with at least one reporter reagent for detecting an analyte, wherein the reporter reagent comprises an affinity component, a linking component, and a reporter component;

determining presence or absence of a signal generated from the contacting, wherein the signal is indicative of presence of the analyte in the sample; and sensing the analyte based upon presence or absence of the generated signal wherein the signal is not detected above background in the absence of the analyte, wherein the linking component comprises a Protein L linker that comprises Protein L or a fragment or derivative thereof, and wherein the Protein L linker comprises a modification permitting or enhancing chemical attachment of the linker to the affinity component.

2. The method of claim 1, wherein the analyte to be detected is a material or a part thereof selected from the group consisting of a protein, a peptide, an antigen, an antibody, a lectin, a lectin-binding carbohydrate, a disease marker, a cytokine, a cytokine receptor, a hormone, a hormone receptor, a cell adhesion molecule, a cell adhesion molecule ligand, a nucleic acid, a sugar chain, a lipid, a cell, a virus, an intracellular organelle, a small molecule, or a low molecular weight compound.

3. The method of claim 1, further wherein the Protein L linker comprises a modification permitting or enhancing chemical attachment of the linker to the reporter component.

4. The method of claim 1, wherein linkage of the Protein L linker to the reporter component comprises a chemical linkage.

5. The method of claim 1, wherein the Protein L linker is linked to the reporter component as a fusion protein.

6. The method of claim 1, wherein linkage of the Protein L linker to the reporter component comprises a noncovalent interaction.

7. The method of claim 1, wherein linkage of the Protein L linker to the reporter component comprises a biotin-streptavidin conjugation.

8. The method of claim 1, wherein linkage of the Protein L linker to the affinity component comprises self-assembly.

9. The method of claim 1, wherein the contacting step comprises contacting the sample with at least two reporter reagents, wherein the reporter reagents in combination constitute a multiplex reporter system, wherein generation of a signal comprises interaction between the two reporter reagents without binding between the linking components of the at least two reagents.

10. The method of claim 2, wherein the affinity component comprises an antibody or a fragment or derivative thereof.

11. The method of claim 2, wherein the reporter component comprises a component selected from a group consisting of a fluorescent material, an enzyme, an enzyme fragment, an enzyme subunit, a receptor, a ligand, a fluorescent protein, a luminescent protein, a non-protein fluorophore, a non-protein chemiluminescent compound, a fluorophore-labeled protein, a fluorescent nanocrystal, a fluorescent chelate, a photosensitizer dye, and a fluorescence quencher.

12. The method of claim 2, wherein detection of the analyte is carried out in a homogeneous system.

13. The method of claim 2, wherein the signal is an optical signal.

14. The method of claim 8, wherein the self assembly is via hydrogen bonding, salt bridging, or a combination thereof.

15. The method of claim 12, wherein the optical signal is generated as a result of FRET, LRET, BRET, enzyme fragment complementation, TR-FRET, or Luminescent Oxygen Channeling.

16. The method of claim 12, wherein detection of the signal does not require instrumentation.

17. The method of claim 9, and wherein each of the at least two reporter reagents comprises a distinct affinity component, such that the distinct affinity components each have an affinity for a different portion of a same analyte.

18. A method of sensing an analyte, comprising the steps of providing a biological sample;

contacting the sample with at least one reporter reagent for detecting an analyte, wherein the reporter reagent comprises an affinity component, a linking component, and a reporter component;

determining presence or absence of a signal generated from the contacting, wherein the signal is indicative of presence of the analyte in the sample; and sensing the analyte based upon presence or absence of the generated signal wherein the signal is not detected above background in the absence of the analyte, wherein the linking component comprises a Protein L linker that comprises Protein L or a fragment or derivative thereof, and wherein the Protein L linker comprises a polypeptide encoded by a polynucleotide having the sequence of SEQ ID NO: 2.

19. A method of sensing an analyte, comprising the steps of providing a biological sample;

contacting the sample with at least one reporter reagent for detecting an analyte, wherein the reporter reagent comprises an affinity component, a linking component, and a reporter component;

determining presence or absence of a signal generated from the contacting, wherein the signal is indicative of presence of the analyte in the sample; and sensing the analyte based upon presence or absence of the generated signal wherein the signal is not detected above background in the absence of the analyte, wherein the linking component comprises a Protein L linker that comprises Protein L or a fragment or derivative thereof, and wherein linkage of the Protein L linker to the affinity component comprises photocrosslinking.

* * * * *

SEQUENCE LISTING

```
<160> NUMBER OF SEQ ID NOS: 10

<210> SEQ ID NO 1
<211> LENGTH: 219
<212> TYPE: DNA
<213> ORGANISM: Artificial Sequence
<220> FEATURE:
<223> OTHER INFORMATION: Recombinant Nucleic Acid Sequence - Protein L
      from Peptostreptococcus magnum with histidine tag and
      Y47W mutation

<400> SEQUENCE: 1

atgcatcatc atcatcatca tgccatggaa gaagtaacaa tcaaagctaa cctaatcttt      60

gcaaatggat ccacacaaac tgcagaattc aaaggaacat ttgaaaaagc aactagtgaa     120

gcttatgcat atgcagatac tttgaagaaa gacaatggag aatggactgt cgacgttgca     180

gataaaggtt atactttaaa tattaaattt gctggatag                             219
```

-continued

<210> SEQ ID NO 2
<211> LENGTH: 219
<212> TYPE: DNA
<213> ORGANISM: Artificial Sequence
<220> FEATURE:
<223> OTHER INFORMATION: Recombinant Nucleic Acid Sequence - Protein L from Peptostreptococcus magnum with histidine tag, Y47W mutation and A20C mutation

<400> SEQUENCE: 2
atgcatcatc atcatcatca tgccatggaa gaagtaacaa tcaaagctaa cctaatcttt 60
gcaaatggat ccacacaaac ttgcgaattc aaaggaacat ttgaaaaagc aactagtgaa 120
gcttatgcat atgcagatac tttgaagaaa gacaatggag aatggactgt cgacgttgca 180
gataaaggtt atactttaaa tattaaattt gctggatag 219

<210> SEQ ID NO 3
<211> LENGTH: 219
<212> TYPE: DNA
<213> ORGANISM: Artificial Sequence
<220> FEATURE:
<223> OTHER INFORMATION: Recombinant Nucleic Acid Sequence - Protein L from Peptostreptococcus magnum with histidine tag, Y47W mutation and T30C mutation

<400> SEQUENCE: 3
atgcatcatc atcatcatca tgccatggaa gaagtaacaa tcaaagctaa cctaatcttt 60
gcaaatggat ccacacaaac tgcagaattc aaaggaacat ttgaaaaagc atgcagtgaa 120
gcttatgcat atgcagatac tttgaagaaa gacaatggag aatggactgt cgacgttgca 180
gataaaggtt atactttaaa tattaaattt gctggatag 219

<210> SEQ ID NO 4
<211> LENGTH: 219
<212> TYPE: DNA
<213> ORGANISM: Artificial Sequence
<220> FEATURE:
<223> OTHER INFORMATION: Recombinant Nucleic Acid Sequence - Protein L from Peptostreptococcus magnum with histidine tag, Y47W mutation and T39 mutation to the Amber STOP codon

<400> SEQUENCE: 4
atgcatcatc atcatcatca tgccatggaa gaagtaacaa tcaaagctaa cctaatcttt 60
gcaaatggat ccacacaaac tgcagaattc aaaggaacat ttgaaaaagc aactagtgaa 120
gcttatgcat atgcagatta gttgaagaaa gacaatggag aatggactgt cgacgttgca 180
gataaaggtt atactttaaa tattaaattt gctggatag 219

<210> SEQ ID NO 5
<211> LENGTH: 219
<212> TYPE: DNA
<213> ORGANISM: Artificial Sequence
<220> FEATURE:
<223> OTHER INFORMATION: Recombinant Nucleic Acid Sequence - Protein L from Peptostreptococcus magnum with histidine tag, Y47W mutation and K41 mutation to the Amber STOP codon

<400> SEQUENCE: 5
atgcatcatc atcatcatca tgccatggaa gaagtaacaa tcaaagctaa cctaatcttt 60
gcaaatggat ccacacaaac tgcagaattc aaaggaacat ttgaaaaagc aactagtgaa 120

-continued

```
gcttatgcat atgcagatac tttgtagaaa gacaatggag aatggactgt cgacgttgca    180

gataaaggtt atactttaaa tattaaattt gctggatag                           219


<210> SEQ ID NO 6
<211> LENGTH: 72
<212> TYPE: PRT
<213> ORGANISM: Artificial Sequence
<220> FEATURE:
<221> NAME/KEY: SITE
<222> LOCATION: (-8)...(-1)
<223> OTHER INFORMATION: Histidine tag
<220> FEATURE:
<223> OTHER INFORMATION: Recombinant Amino Acid Sequence - Protein L
      from Peptostreptococcus magnum with histidine tag and
      Y47W mutation

<400> SEQUENCE: 6

Met His His His His His His Ala Met Glu Glu Val Thr Ile Lys Ala
            -5                  1               5

Asn Leu Ile Phe Ala Asn Gly Ser Thr Gln Thr Ala Glu Phe Lys Gly
    10                  15                  20

Thr Phe Glu Lys Ala Thr Ser Glu Ala Tyr Ala Tyr Ala Asp Thr Leu
25                  30                  35                  40

Lys Lys Asp Asn Gly Glu Trp Thr Val Asp Val Ala Asp Lys Gly Tyr
                45                  50                  55

Thr Leu Asn Ile Lys Phe Ala Gly
            60


<210> SEQ ID NO 7
<211> LENGTH: 72
<212> TYPE: PRT
<213> ORGANISM: Artificial Sequence
<220> FEATURE:
<221> NAME/KEY: SITE
<222> LOCATION: (-8)...(-1)
<223> OTHER INFORMATION: Histidine tag
<220> FEATURE:
<223> OTHER INFORMATION: Recombinant Amino Acid Sequence - Protein L
      from Peptostreptococcus magnum with histidine tag, Y47W
      mutation and A20C mutation

<400> SEQUENCE: 7

Met His His His His His His Ala Met Glu Glu Val Thr Ile Lys Ala
            -5                  1               5

Asn Leu Ile Phe Ala Asn Gly Ser Thr Gln Thr Cys Glu Phe Lys Gly
    10                  15                  20

Thr Phe Glu Lys Ala Thr Ser Glu Ala Tyr Ala Tyr Ala Asp Thr Leu
25                  30                  35                  40

Lys Lys Asp Asn Gly Glu Trp Thr Val Asp Val Ala Asp Lys Gly Tyr
                45                  50                  55

Thr Leu Asn Ile Lys Phe Ala Gly
            60


<210> SEQ ID NO 8
<211> LENGTH: 72
<212> TYPE: PRT
<213> ORGANISM: Artificial Sequence
<220> FEATURE:
<221> NAME/KEY: SITE
<222> LOCATION: (-8)...(-1)
<223> OTHER INFORMATION: Histidine tag
<220> FEATURE:
<223> OTHER INFORMATION: Recombinant Amino Acid Sequence - Protein L
      from Peptostreptococcus magnum with histidine tag, Y47W
      mutation and T30C mutation
```

-continued

<400> SEQUENCE: 8

```
Met His His His His His His Ala Met Glu Glu Val Thr Ile Lys Ala
            -5                  1               5

Asn Leu Ile Phe Ala Asn Gly Ser Thr Gln Thr Ala Glu Phe Lys Gly
    10                  15                  20

Thr Phe Glu Lys Ala Cys Ser Glu Ala Tyr Ala Tyr Ala Asp Thr Leu
25                  30                  35                  40

Lys Lys Asp Asn Gly Glu Trp Thr Val Asp Val Ala Asp Lys Gly Tyr
                45                  50                  55

Thr Leu Asn Ile Lys Phe Ala Gly
            60
```

<210> SEQ ID NO 9
<211> LENGTH: 72
<212> TYPE: PRT
<213> ORGANISM: Artificial Sequence
<220> FEATURE:
<221> NAME/KEY: SITE
<222> LOCATION: (-8)...(-1)
<223> OTHER INFORMATION: Histidine tag
<220> FEATURE:
<221> NAME/KEY: VARIANT
<222> LOCATION: 39
<223> OTHER INFORMATION: Xaa = p-benzyl-L-phenylalanine (Bpa)
<220> FEATURE:
<223> OTHER INFORMATION: Recombinant Amino Acid Sequence - Protein L from Peptostreptococcus magnum with histidine tag, Y47W mutation and T39 mutation to the Amber STOP codon for incorporation of Bpa

<400> SEQUENCE: 9

```
Met His His His His His His Ala Met Glu Glu Val Thr Ile Lys Ala
            -5                  1               5

Asn Leu Ile Phe Ala Asn Gly Ser Thr Gln Thr Ala Glu Phe Lys Gly
    10                  15                  20

Thr Phe Glu Lys Ala Thr Ser Glu Ala Tyr Ala Tyr Ala Asp Xaa Leu
25                  30                  35                  40

Lys Lys Asp Asn Gly Glu Trp Thr Val Asp Val Ala Asp Lys Gly Tyr
                45                  50                  55

Thr Leu Asn Ile Lys Phe Ala Gly
            60
```

<210> SEQ ID NO 10
<211> LENGTH: 72
<212> TYPE: PRT
<213> ORGANISM: Artificial Sequence
<220> FEATURE:
<221> NAME/KEY: SITE
<222> LOCATION: (-8)...(-1)
<223> OTHER INFORMATION: Histidine tag
<220> FEATURE:
<221> NAME/KEY: VARIANT
<222> LOCATION: 41
<223> OTHER INFORMATION: Xaa = p-benzyl-L-phenylalanine (Bpa)
<220> FEATURE:
<223> OTHER INFORMATION: Recombinant Amino Acid Sequence - Protein L from Peptostreptococcus magnum with histidine tag, Y47W mutation and K41 mutation to the Amber STOP codon for incorporation of Bpa

<400> SEQUENCE: 10

```
Met His His His His His His Ala Met Glu Glu Val Thr Ile Lys Ala
            -5                  1               5

Asn Leu Ile Phe Ala Asn Gly Ser Thr Gln Thr Ala Glu Phe Lys Gly
    10                  15                  20
```

-continued

```
Thr Phe Glu Lys Ala Thr Ser Glu Ala Tyr Ala Tyr Ala Asp Thr Leu
25                  30                  35                  40

Xaa Lys Asp Asn Gly Glu Trp Thr Val Asp Val Ala Asp Lys Gly Tyr
                45                  50                  55

Thr Leu Asn Ile Lys Phe Ala Gly
            60
```